(12) United States Patent
Nyuli et al.

(10) Patent No.: US 10,631,984 B2
(45) Date of Patent: Apr. 28, 2020

(54) TRANSSEPTAL DELIVERY SYSTEM

(71) Applicant: Neovasc Tiara Inc., Richmond (CA)

(72) Inventors: Colin A. Nyuli, Vancouver (CA);
Randy Matthew Lane, Langley (CA);
Karen Tsoek-Ji Wong, Richmond (CA)

(73) Assignee: Neovasc Tiara Inc., Richmond, British Columbia ( * ) Notice: Subject to any disclaimer, the term of this patent is extended or adjusted under 35 U.S.C. 154(b) by 146 days.

(21) Appl. No.: 15/379,748

(22) Filed: Dec. 15, 2016

(65) Prior Publication Data

US 2017/0165064 A1 Jun. 15, 2017

Related U.S. Application Data

(60) Provisional application No. 62/267,722, filed on Dec. 15, 2015.

(51) Int. Cl.
*A61F 2/24* (2006.01)
*A61F 2/95* (2013.01)
(Continued)

(52) U.S. Cl.
CPC .......... *A61F 2/2436* (2013.01); *A61F 2/2418* (2013.01); *A61F 2/2427* (2013.01);
(Continued)

(58) Field of Classification Search
CPC ...... A61F 2/2427; A61F 2/243; A61F 2/2436; A61F 2/2439; A61F 2/97; A61F 2/95;
(Continued)

(56) References Cited

U.S. PATENT DOCUMENTS 5,415,664 A * 5/1995 Pinchuk .................. A61F 2/95
604/523
8,579,964 B2 11/2013 Lane et al.
(Continued)

FOREIGN PATENT DOCUMENTS

CA 3007660 A1 6/2017
CN 101553190 A 10/2009
(Continued)

OTHER PUBLICATIONS

"International Application Serial No. PCT/CA2016/051482, International Preliminary Report on Patentability dated Jun. 28, 2018", 10 pgs.
(Continued)

*Primary Examiner* — Darwin P Erezo
*Assistant Examiner* — Katherine H Schwiker
(74) *Attorney, Agent, or Firm* — Schwegman Lundberg & Woessner, P.A.

(57) ABSTRACT

A delivery system includes a delivery catheter with a capsule configured to carry a prosthesis and a steering catheter for steering the delivery catheter. The delivery catheter can be advanced through a patient's vasculature to a target treatment area. The capsule can be opened and the prosthesis can be deployed into the target treatment area. Additionally, a method for delivering a prosthesis to a target treatment area includes advancing a delivery catheter through a patient's vasculature to the target treatment area, steering the delivery catheter toward the target treatment area, opening a capsule on the delivery catheter, and deploying the prosthesis into the target treatment area.

24 Claims, 21 Drawing Sheets

(51) Int. Cl.
*A61M 25/00* (2006.01)
*A61M 25/01* (2006.01)
*A61M 25/09* (2006.01)
*A61F 2/97* (2013.01)

(52) U.S. Cl.
CPC .... *A61M 25/0054* (2013.01); *A61M 25/0074* (2013.01); *A61M 25/0133* (2013.01); *A61M 25/09* (2013.01); *A61F 2/97* (2013.01); *A61F 2002/9517* (2013.01)

(58) Field of Classification Search
CPC .......... A61F 2/962; A61F 2/966; A61F 2/958; A61F 2/954; A61F 2002/9517; A61F 2002/9505; A61F 2002/9511; A61F 2002/9583; A61F 2002/9586; A61F 2002/9522; A61F 2002/9528; A61F 2002/9534; A61F 2002/9665; A61F 2/2433
USPC ....................................................... 623/2.11
See application file for complete search history.

(56) References Cited

U.S. PATENT DOCUMENTS

| | | | |
|---|---|---|---|
| 2008/0065011 A1* | 3/2008 | Marchand | A61F 2/2433 604/103.02 |
| 2009/0234443 A1 | 9/2009 | Ottma et al. | |
| 2013/0274870 A1* | 10/2013 | Lombardi | A61F 2/2418 623/2.11 |
| 2014/0155990 A1 | 6/2014 | Nyuli et al. | |
| 2014/0172086 A1 | 6/2014 | Quadri et al. | |
| 2014/0200649 A1* | 7/2014 | Essinger | A61F 2/2436 623/1.12 |
| 2015/0306358 A1 | 10/2015 | Duffy et al. | |
| 2015/0342736 A1 | 12/2015 | Rabito et al. | |

FOREIGN PATENT DOCUMENTS

| | | |
|---|---|---|
| CN | 103118630 A | 5/2013 |
| CN | 108601645 A | 9/2018 |
| EP | 3389557 A1 | 10/2018 |
| WO | WO-2010045297 A2 | 4/2010 |
| WO | WO-2011126758 A1 | 10/2011 |
| WO | WO-2013056898 A1 | 4/2013 |
| WO | WO-2013075215 A1 | 5/2013 |
| WO | WO-2015038875 A1 | 3/2015 |
| WO | WO-2017100927 A1 | 6/2017 |

OTHER PUBLICATIONS

"International Application Serial No. PCT/CA2016/051482, Written Opinion dated Feb. 27, 2017", 8 pgs.

International Search Report dated Feb. 27, 2017 for International Application No. PCT/CA2016/051482.

"European Application Serial No. 16874205.4, Extended European Search Report dated Jul. 5, 2019", 9 pgs.

"Chinese Application Serial No. 201680081812.0, Office Action dated Oct. 31, 2019", w/ English Translation, 22 pgs.

"European Application Serial No. 16874205.4, Response filed Feb. 3, 2020 to Extended European Search Report dated Jul. 5, 2019", 17 pgs.

* cited by examiner

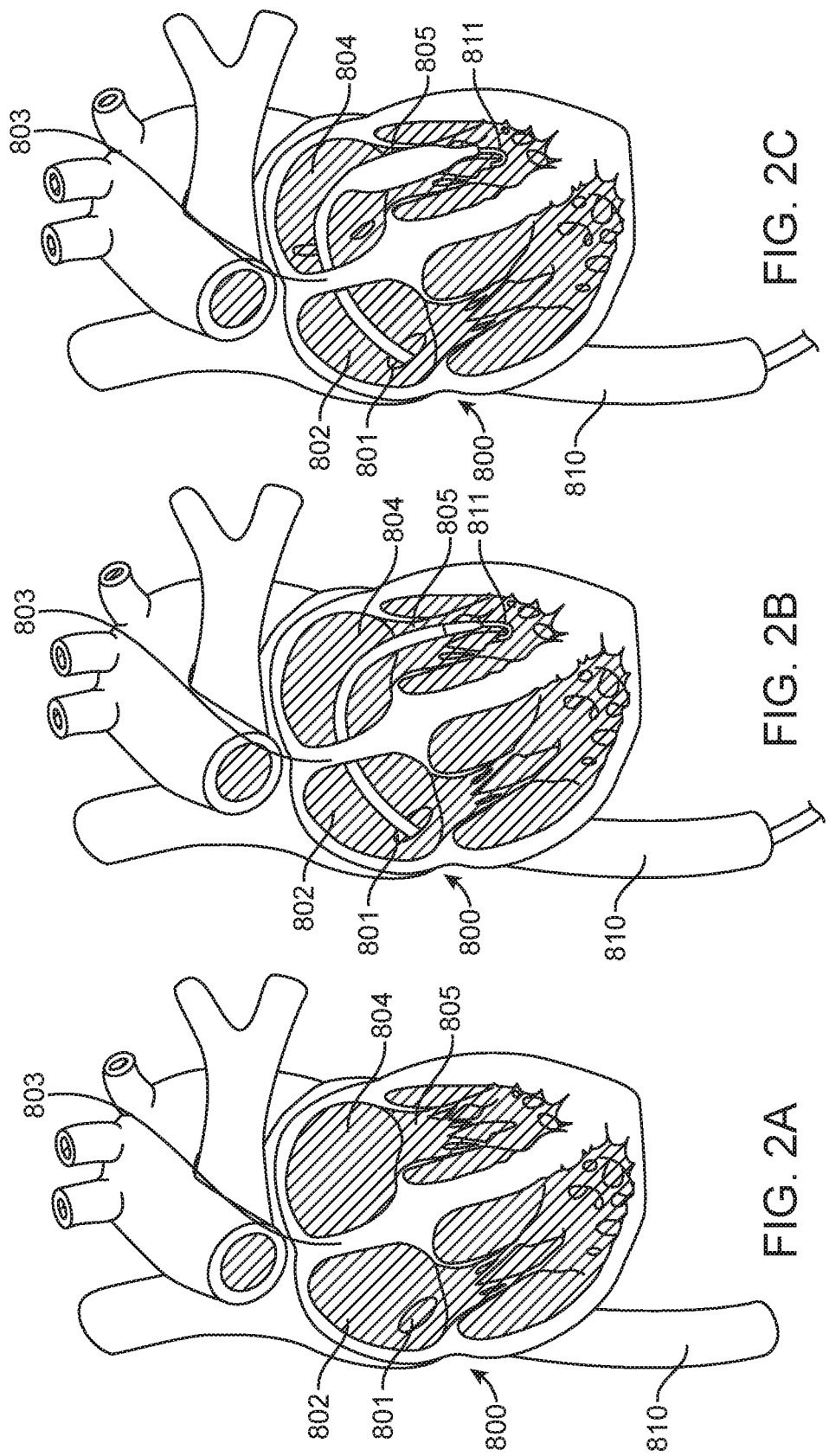

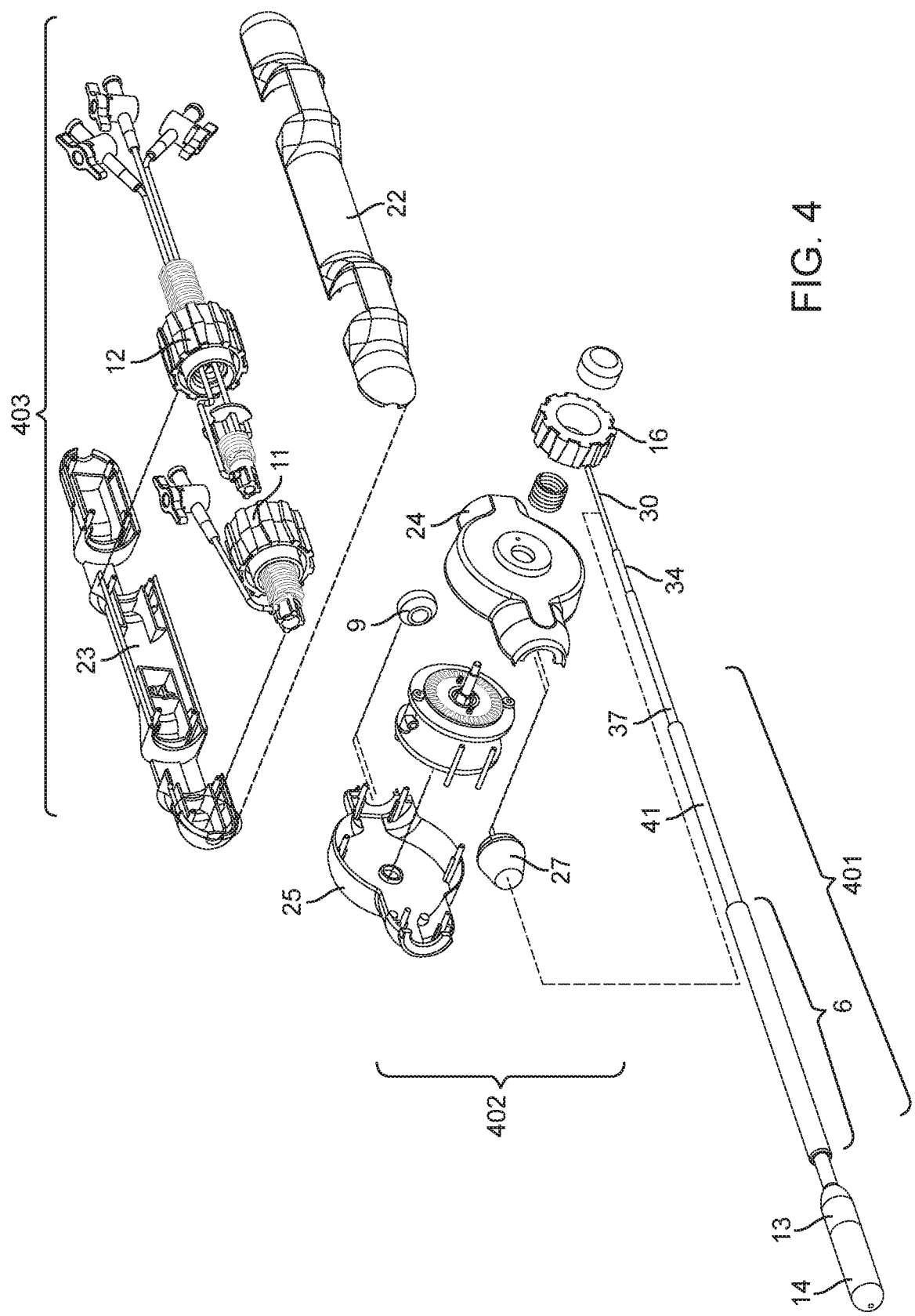

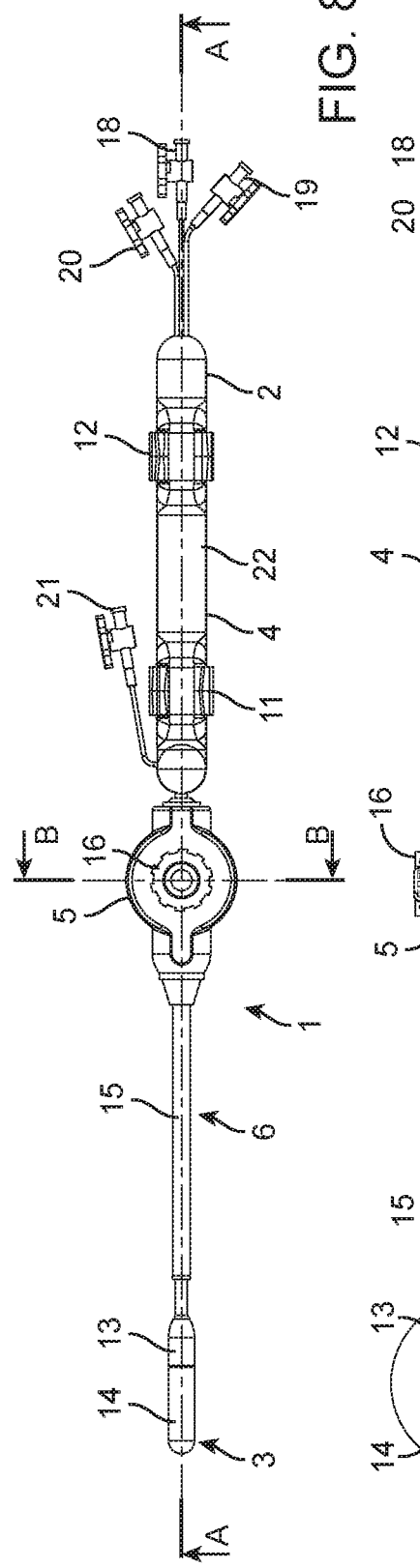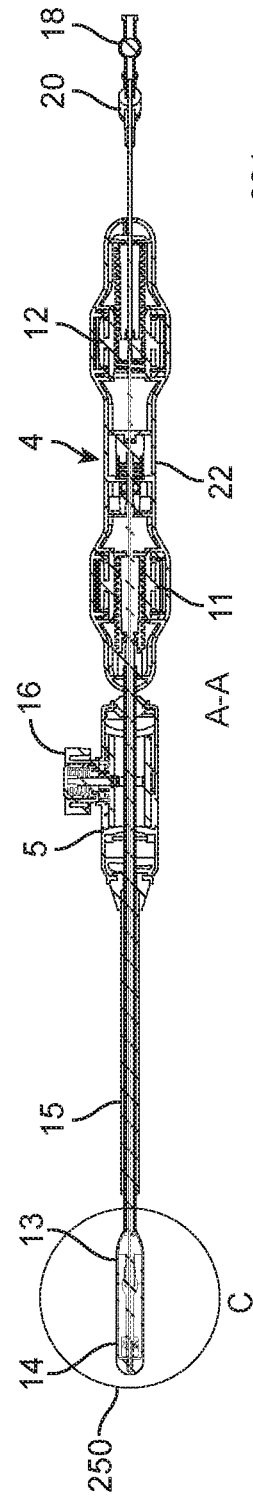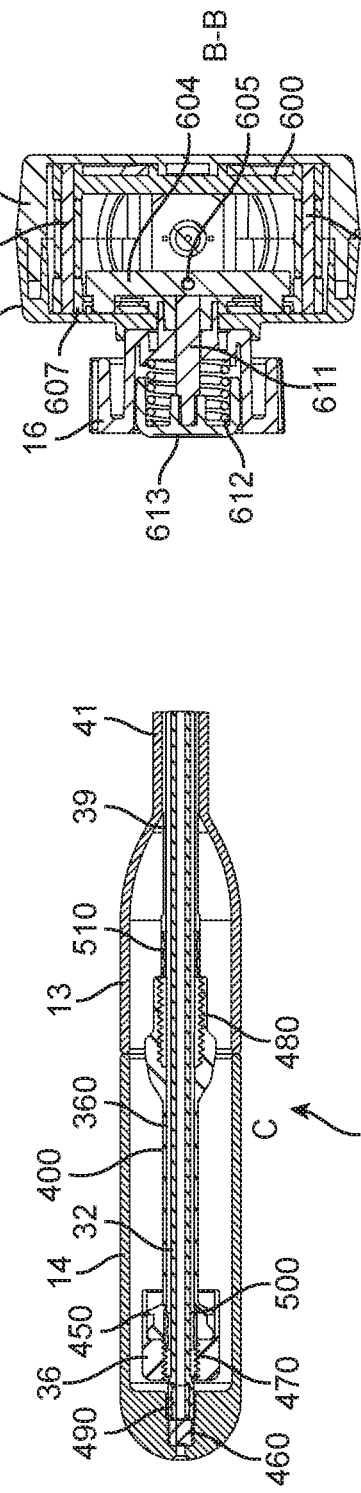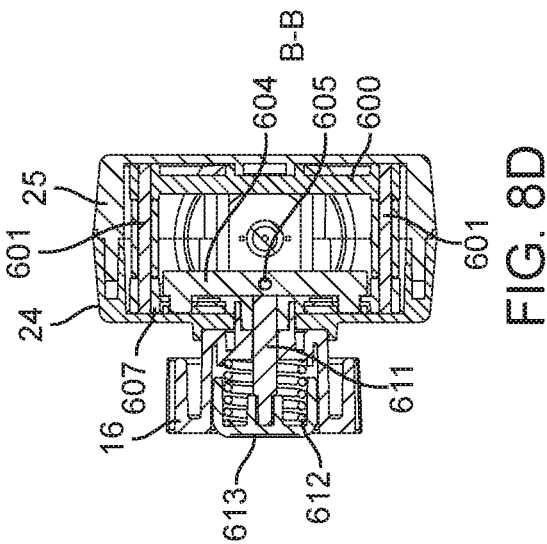

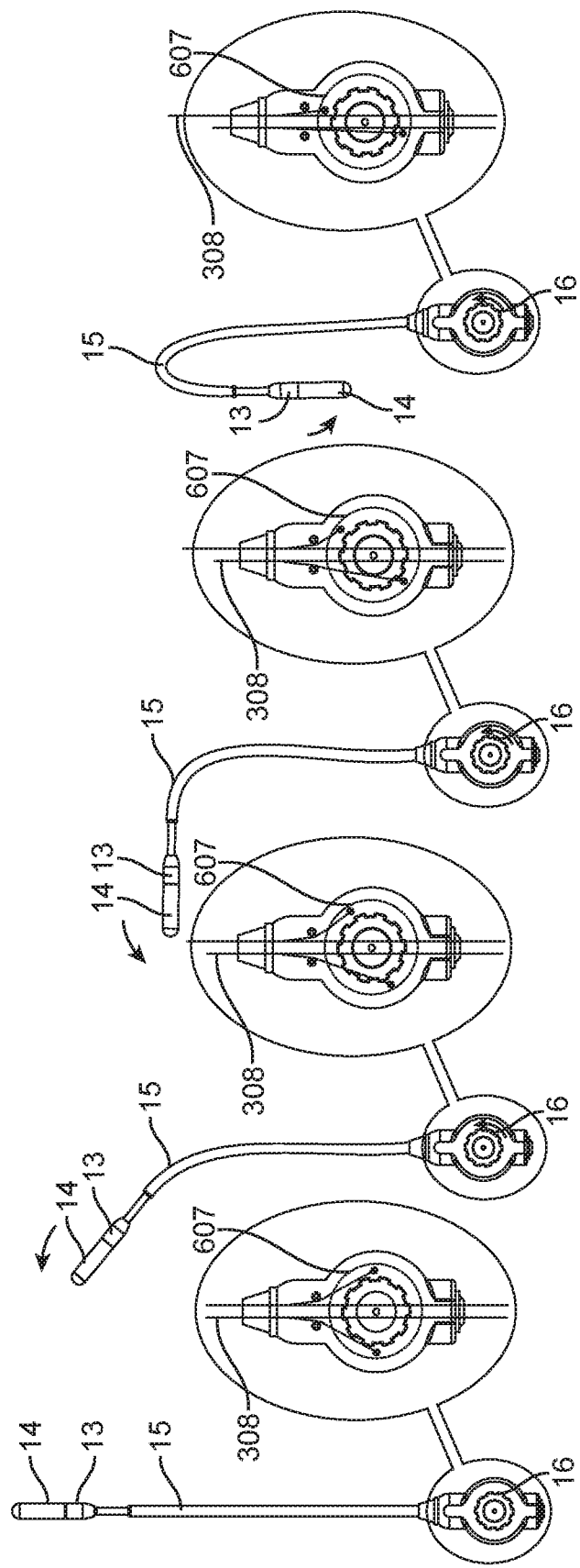

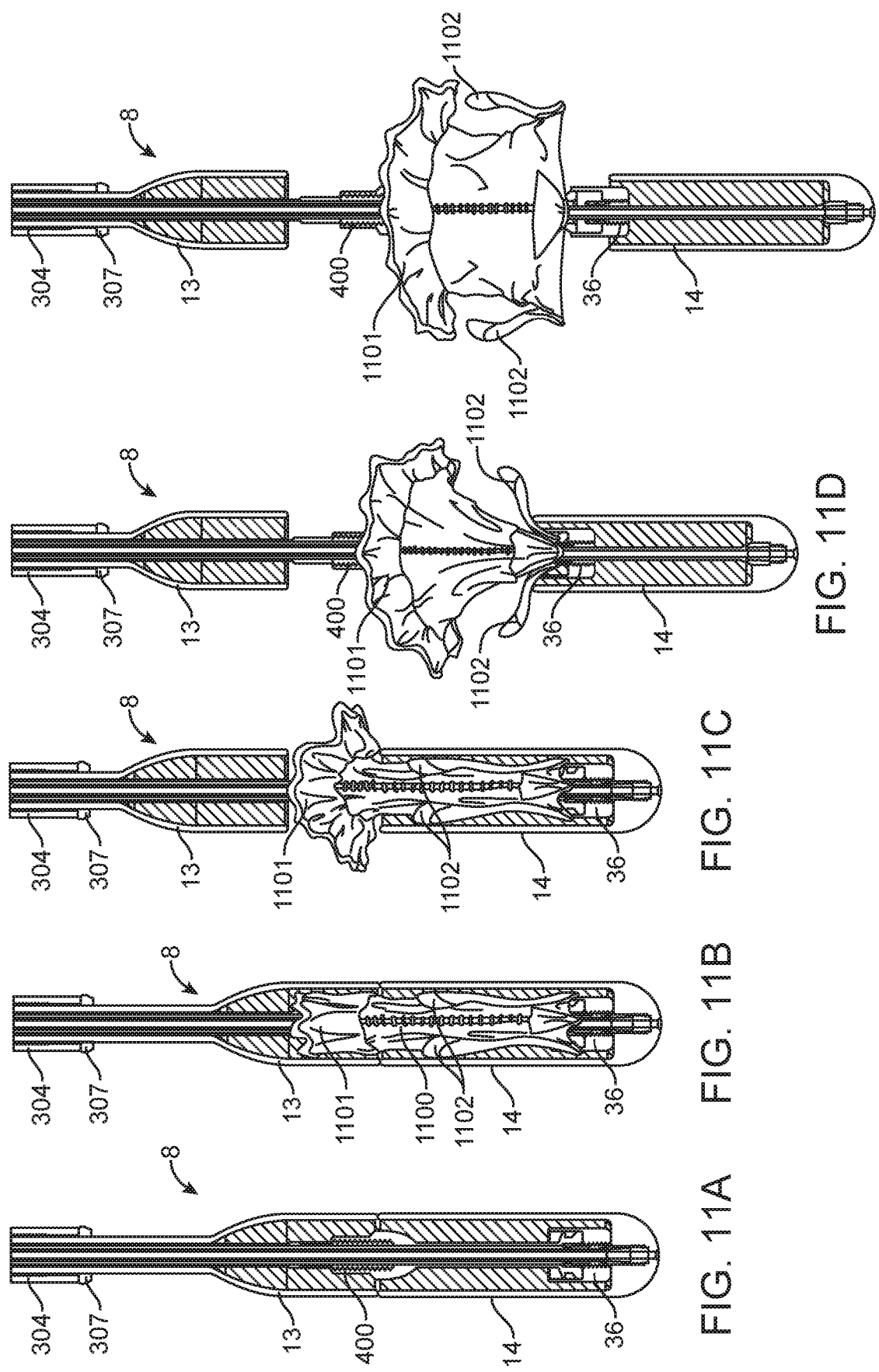

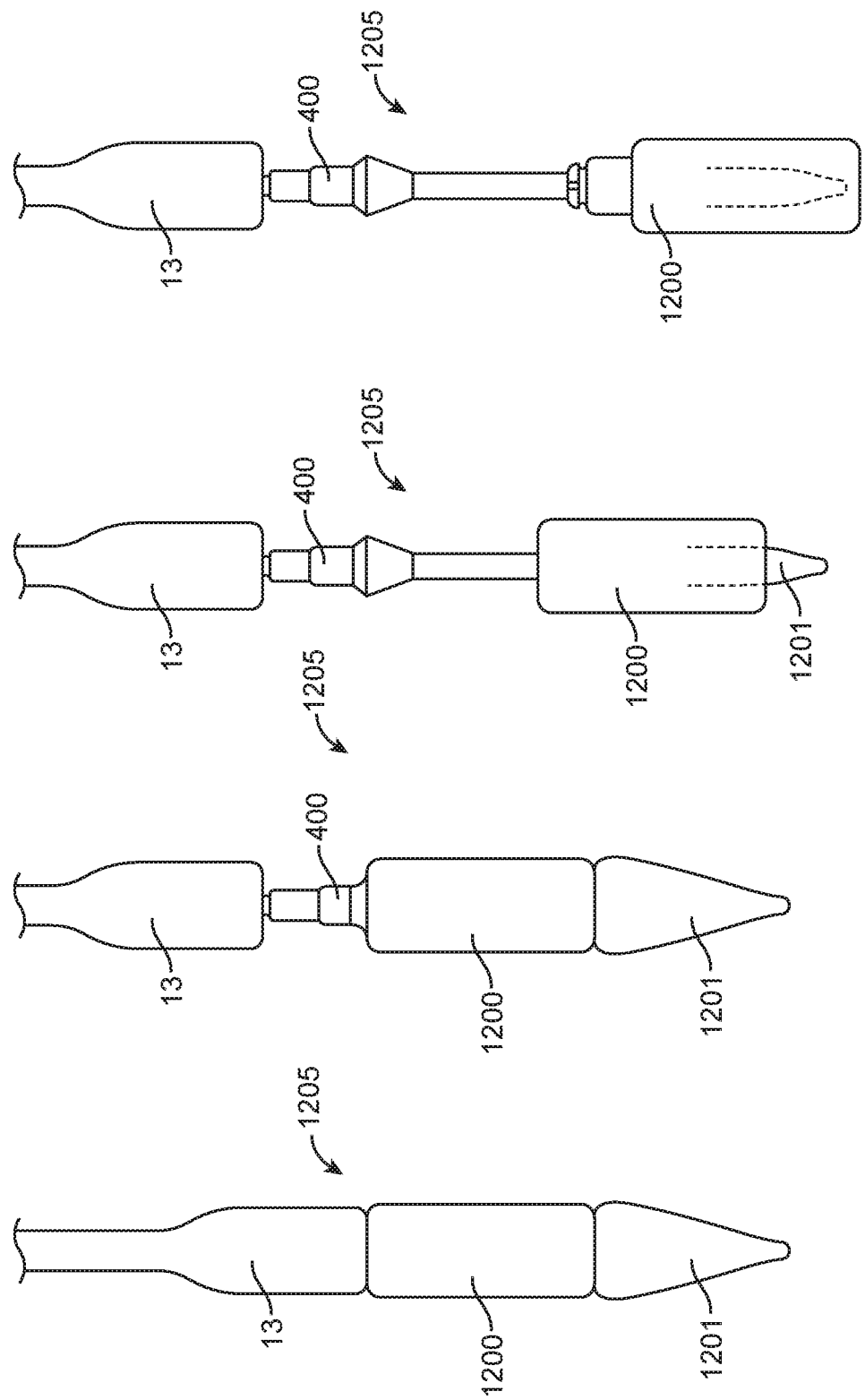

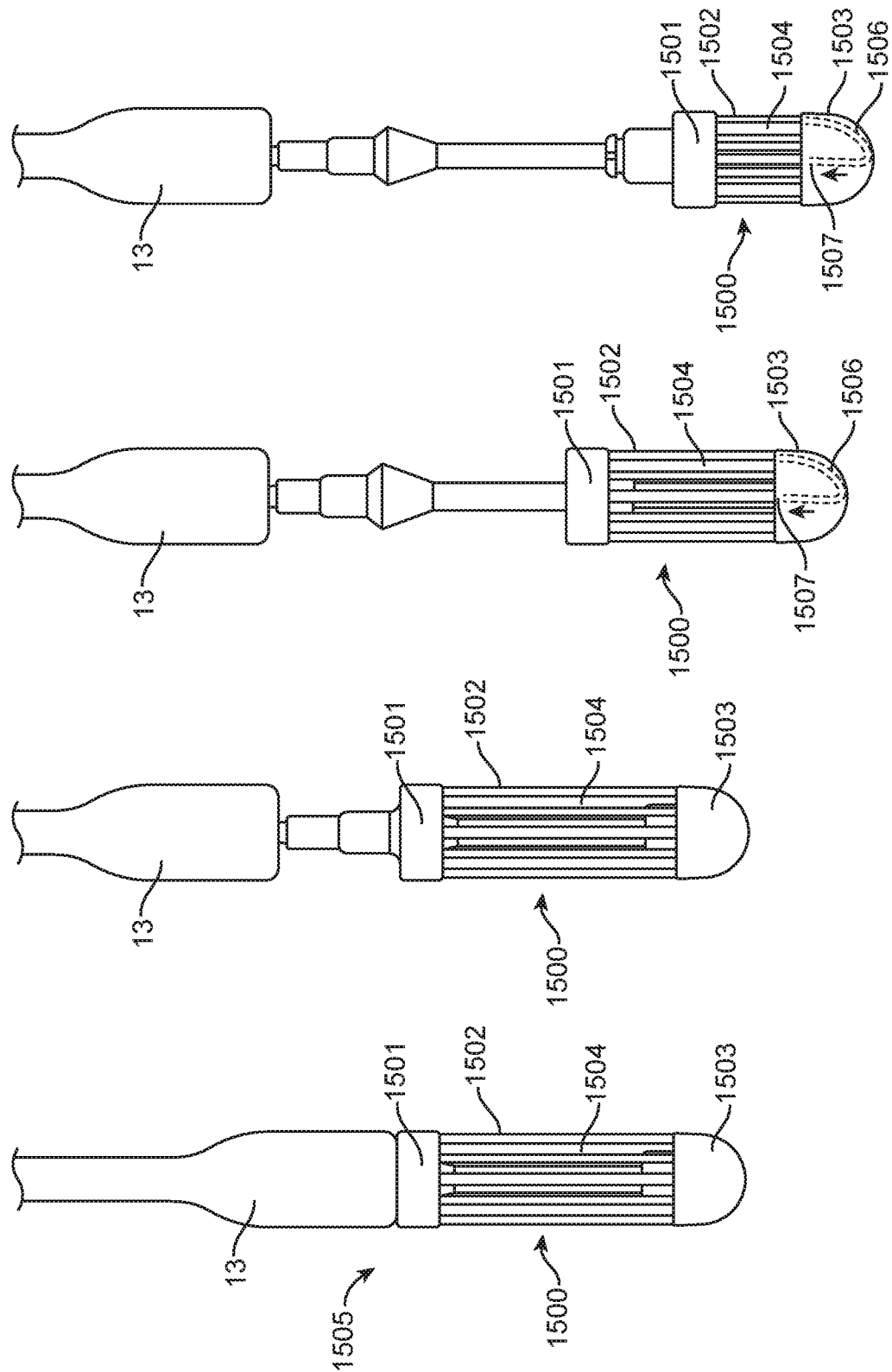

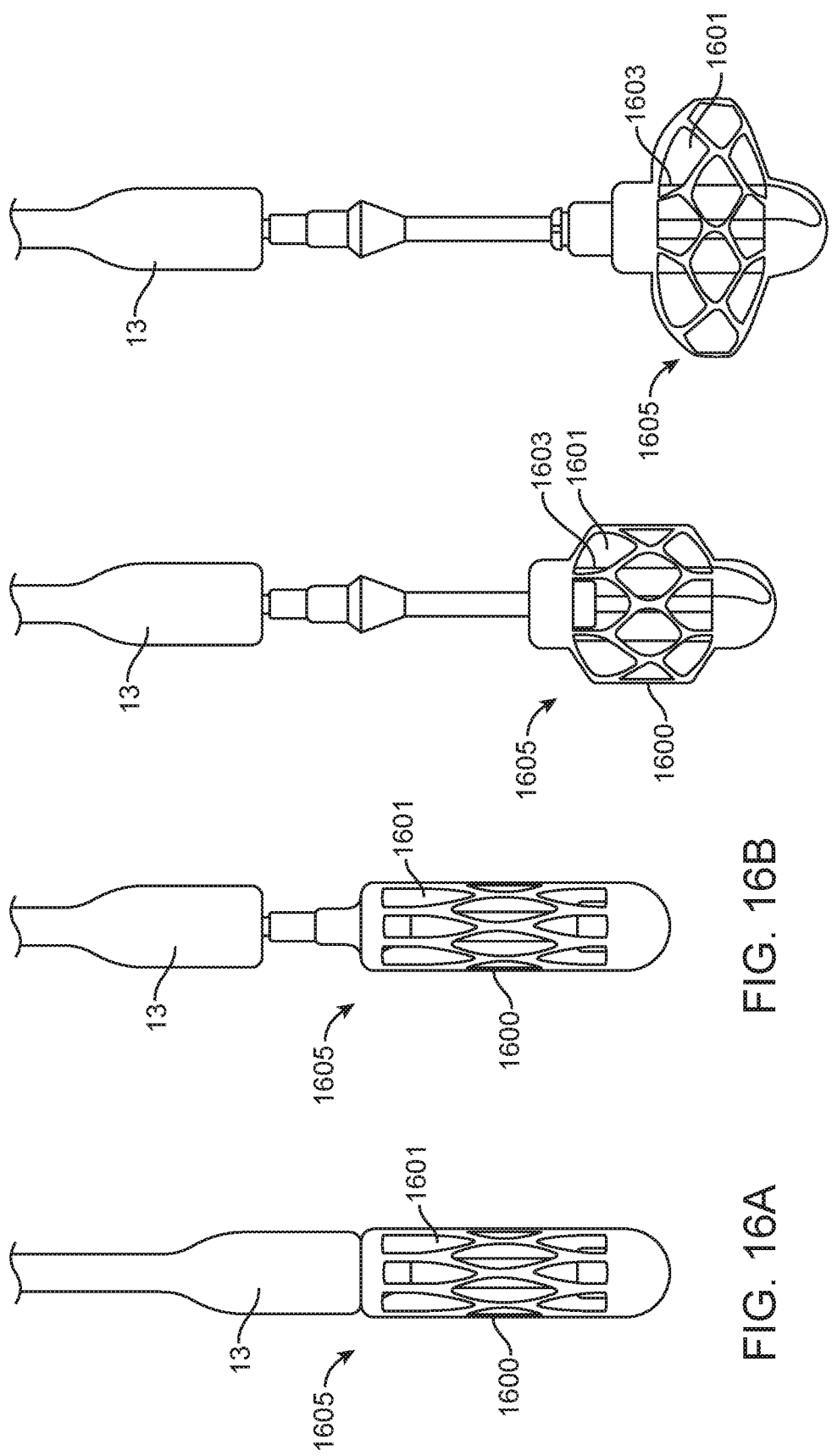

TRANSSEPTAL DELIVERY SYSTEM

CROSS-REFERENCE

The present application is a non-provisional of, and claims the benefit of U.S. Provisional Patent Application No. 62/267,722 filed Dec. 15, 2015; the entire contents of which are incorporated herein by reference.

The present application is related to U.S. patent application Ser. No. 13/096,572, now U.S. Pat. No. 8,579,964, filed Apr. 28, 2011; the entire contents of which are incorporated herein by reference.

BACKGROUND OF THE INVENTION

1. Field of the Invention

The present invention generally relates to medical devices and methods, and more particularly relates to prosthesis delivery systems used in the treatment of valve insufficiency, such as mitral insufficiency, also referred to as mitral regurgitation.

The heart of vertebrate animals is divided into four chambers, and is equipped with four valves (the mitral, aortic, pulmonary and tricuspid valves) that ensure that blood pumped by the heart flows in a forward direction through the cardiovascular system. The mitral valve of a healthy heart prevents the backflow of blood from the left ventricle into the left atrium of the heart, and comprises two flexible leaflets (anterior and posterior) that close when the left ventricle contracts. The leaflets are attached to a fibrous annulus, and their free edges are tethered by subvalvular chordae tendineae to papillary muscles in the left ventricle to prevent them from prolapsing into the left atrium during the contraction of the left ventricle.

Various cardiac diseases or degenerative changes may cause dysfunction in any of these portions of the mitral valve apparatus, causing the mitral valve to become abnormally narrowed or dilated, or to allow blood to leak (i.e. regurgitate) from the left ventricle back into the left atrium. Any such impairments compromise cardiac sufficiency, and can be debilitating or life threatening.

Numerous surgical methods and devices have accordingly been developed to treat mitral valve dysfunction, including open-heart surgical techniques for replacing, repairing or reshaping the native mitral valve apparatus, and the surgical implantation of various prosthetic devices such as annuloplasty rings to modify the anatomy of the native mitral valve. However, these devices require open heart surgery which requires a lengthy recovery period for the patient and is costly. More recently, less invasive transapical and transcatheter techniques for the delivery of replacement mitral valve assemblies have been developed. In such techniques, a prosthetic valve is generally mounted in a crimped state on the end of a flexible catheter or delivery system and advanced through a blood vessel or the body of the patient until the valve reaches the implantation site. The prosthetic valve is then expanded to its functional size at the site of the defective native valve.

While these devices and methods are promising treatments for valvar insufficiency, they can be difficult to deliver, expensive to manufacture, or may not be indicated for all patients. Additionally some of the delivery systems have large sizes which create large entry wounds in the body. Therefore, it would be desirable to provide improved devices and methods for the treatment of valvar insufficiency such as mitral insufficiency. It would be desirable if such delivery devices had smaller profiles, were easily advanced or steered to the target treatment site, and allowed accurate delivery and deployment of the prosthesis At least some of these objectives will be met by the devices and methods disclosed below.

2. Description of the Background Art

US Patent Publication No. 2015/0342736 describes a prosthetic valve delivery system.

SUMMARY OF THE INVENTION

The present invention generally relates to medical systems, devices and methods, and more particularly relates to prosthesis delivery systems used in the treatment of valve insufficiency, such as mitral insufficiency, also referred to as mitral regurgitation.

In one aspect, a delivery system for delivering a prosthesis to a target treatment area comprises an inner guidewire catheter, a distal capsule coupled to the distal end of the inner guidewire catheter, and a sheath catheter slidably disposed over the inner guidewire catheter, the sheath catheter having a proximal end and a distal end. The delivery system can further comprise a proximal capsule coupled to the distal end of the sheath catheter and an actuator mechanism operably coupled with the inner guidewire catheter and the sheath catheter. The inner guidewire catheter can have a proximal end, a distal end, and a lumen extending therebetween, the lumen sized to slidably receive a guidewire and the distal capsule can comprise an inner channel sized to receive the prosthesis. The proximal capsule can also comprise an inner channel sized to receive the prosthesis. Additionally, actuation of the actuator mechanism in a first direction can move the proximal capsule away from the distal capsule thereby removing a constraint from the prosthesis and allowing the prosthesis to expand while actuation of the actuator mechanism in a second direction opposite the first direction can move the proximal capsule into engagement with the distal capsule thereby enclosing the prosthesis therein.

The delivery system can comprise a bell catheter slidably disposed over the guidewire catheter. The bell catheter can have a bell element disposed adjacent a distal end of the bell catheter. An anchor catheter can be slidably disposed over the bell catheter, the anchor catheter having an anchor element adjacent a distal end of the anchor catheter and configured to engage the prosthesis, and wherein the bell member can constrain the prosthesis into engagement with the anchor element.

The delivery system can comprise a steerable catheter having an actuator mechanism. The inner guidewire catheter and the sheath catheter can be slidably disposed in the steerable catheter, and actuation of the actuator mechanism can steer the steerable catheter, thereby steering the inner guidewire catheter and the sheath catheter. The steerable catheter can comprise a plurality of pull wires coupled to the steerable catheter. Moreover, actuation of the actuator mechanism can move the pull wires thereby steering the steerable catheter.

The actuator mechanism for steering the steerable catheter can comprise a rotatable knob and the delivery system can further comprise a handle coupled to a proximal portion of the delivery system. The actuator mechanism can be coupled to the handle. The actuator mechanism can comprise a plurality of rotatable thumbwheels.

The distal capsule can comprise an expandable member and the expandable member can comprise a stent or a balloon. The distal capsule can comprise a corrugated region. In some embodiments, the distal capsule can comprise a plurality of hinged splines that can be configured to radially expand at a hinge when compression is applied to the plurality of hinged splines. The distal capsule can comprise a proximal portion, a distal portion, and a plurality of filaments, wherein movement of the filaments can move the proximal portion relative to the distal portion thereby increasing or decreasing a length of the distal capsule.

The delivery system can also comprise a prosthesis and the prosthesis can be a prosthetic mitral valve.

In another aspect, a method for delivering a prosthesis to a target treatment area comprises: providing a delivery system having a distal capsule coupled to an inner guidewire catheter and a proximal capsule coupled to a sheath catheter; actuating an actuation mechanism thereby moving the proximal capsule away from the distal capsule; releasing a constraint from a prosthesis disposed in the proximal and distal capsules; and deploying the prosthesis in the target treatment area. In some embodiments, the inner guidewire catheter can be slidably disposed in the sheath catheter, and actuating the actuation mechanism can move the inner guidewire catheter relative to the sheath catheter. In addition, actuating the actuation mechanism can comprise rotating a thumbwheel.

The delivery system can further comprise a bell catheter slidably disposed over the guidewire catheter, wherein the bell catheter can have a bell element disposed adjacent a distal end of the bell catheter, and wherein deploying the prosthesis can comprise moving the bell element away from the prosthesis thereby removing a constraint from the prosthesis.

In some embodiments, the delivery system can comprise an anchor catheter slidably disposed over the bell catheter, wherein the anchor catheter can have an anchor element adjacent a distal end of the anchor catheter and configured to engage the prosthesis, and wherein deploying the prosthesis can comprise moving the bell member away from the anchor element thereby removing a constraint from the prosthesis.

The method for delivering a prosthesis to a target treatment area can comprise steering the delivery system with a steerable catheter disposed over the delivery system. Moreover, steering can comprise actuating an actuator mechanism operably coupled to the steerable catheter and actuating an actuator mechanism can comprise moving a plurality of pull wires coupled to the steerable catheter. In some embodiments, steering can comprise rotating a rotatable knob.

The distal capsule can comprise an expandable member and the method disclosed herein can further comprise radially expanding or radially collapsing the expandable member, which can comprise a stent or a balloon. Additionally, the distal capsule can comprise a corrugated region and the method disclosed herein can further comprise axially expanding or axially collapsing the corrugated region. The distal capsule can also comprise a plurality of hinged splines and the method disclosed herein can further comprise radially expanding the hinged splines by applying compression thereto, or radially collapsing the hinged splines by applying tension thereto. The distal capsule can comprise a proximal portion, a distal portion, and a plurality of filaments, and the method disclosed herein can further comprise moving the filaments thereby moving the distal capsule toward or away from the proximal capsule. The target treatment area can be a native mitral valve and the prosthesis can be a prosthetic mitral valve.

In still another aspect, a delivery system for delivering a prosthesis to a target treatment area, comprises: a delivery catheter for delivering the prosthesis to the target treatment area and a steerable catheter operably coupled with the delivery catheter, the steerable catheter comprising an actuator mechanism, wherein actuation of the actuator mechanism steers the steerable catheter, thereby also steering the delivery catheter.

In some embodiments, the steerable catheter can comprise a plurality of pull wires coupled to the steerable catheter, and actuation of the actuator mechanism can move the pull wires thereby steering the steerable catheter. In addition, the actuator mechanism for steering the steerable catheter can comprise a rotatable knob and the delivery system can further comprise a handle that can be coupled to a proximal portion of the delivery catheter, wherein the actuator mechanism can be coupled to the handle. The delivery system can further comprise a prosthesis, which can be a prosthetic mitral valve.

In another aspect, a method for delivering a prosthesis to a target treatment area comprises: providing a delivery catheter carrying the prosthesis; providing a steering catheter operably coupled to the delivery catheter; actuating an actuation mechanism thereby steering the steering catheter and steering the delivery catheter; and deploying the prosthesis in the target treatment area. Actuating the actuation mechanism can comprise rotating a knob and actuating the actuator mechanism can comprise moving a plurality of pull wires coupled to the steering catheter. The target treatment area can be a native mitral valve and the prosthesis can be a prosthetic mitral valve.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A-2F are sequential views of the procedural pathway traversed by the prosthesis during a trans-septal implantation procedure.

FIG. 4 is an assembly view of the delivery system seen in FIG. 1.

FIG. 8A is a side view of the delivery system in FIG. 1.

FIG. 8B is a cross-sectional view of the delivery system taken along line A-A in FIG. 8A.

FIGS. 8C-8D show other cross-sections of the delivery system.

FIGS. 10A-10D are sequential views of the steering handle portion of the delivery system of FIG. 1.

FIGS. 11A-11E are sequential cross-sectional views of the valve capsule portion taken along the line A-A in FIG. 8A.

FIGS. 12A-12D are sequential partial views of an alternative embodiment of the valve capsule portion of the delivery system of FIG. 1.

FIGS. 15A-15D are sequential partial views of an alternative embodiment of the valve capsule portion of the delivery system of FIG. 1.

FIGS. 16A-16D are sequential partial views of an alternative embodiment of the valve capsule portion of the delivery system of FIG. 1.

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

Trans-Septal Delivery System

Figure 1:
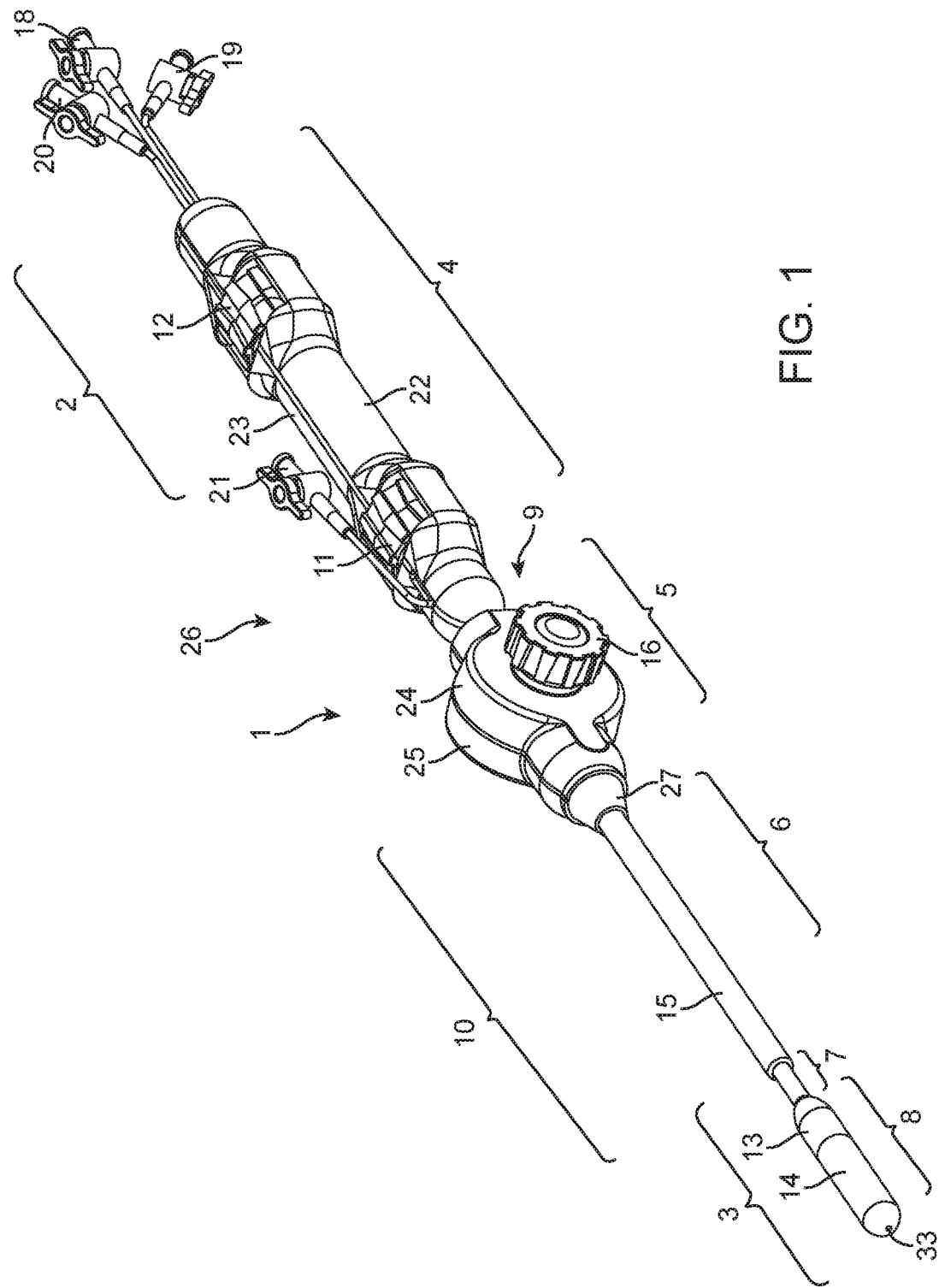
FIG. 1 is a perspective view of a trans-septal delivery system for a prosthetic heart valve.

Referring initially to FIG. 1, one embodiment of a trans-septal delivery system for trans-catheter heart valve delivery is depicted generally as 1. In the drawings and in the descriptions which follow, the term "proximal" will refer to the end 2 of the delivery system that is closest to the user, while the term "distal" will refer to the end 3 that is farthest from the user. The trans-septal delivery system 1 can comprise a prosthesis such as a prosthesis capsule or valve capsule assembly 8, a delivery catheter assembly 7, a steering guide 10, a delivery handle assembly 4, and an interface 9 between the delivery handle 4 and steering handle 5. The steering guide 10 can be comprised of a steerable catheter assembly 6 and a steering handle 5. The valve capsule assembly 8 can be in operable communication with the delivery handle assembly 4 by way of the delivery catheter assembly 7 which extends therebetween. The translational position and angular attitude of the prosthesis or valve capsule assembly 8 can be operably controlled by the steering handle 5 and in communication by way of the steerable catheter assembly 6 which extends therebetween. The interface 9 can be comprised of a slidable seal, such as an o-ring type seal. The interface 9 can further function to allow the delivery handle or delivery catheter to translate within the steering handle while maintaining some stiction, thus preventing blood or other fluid from seeping out of the steering handle should such blood or fluid make its way up the steering catheter assembly.

Further details of a trans-catheter mitral valve or any prosthesis that may be used with any of the delivery devices described herein, along with other related delivery catheters are described in commonly owned U.S. Pat. No. 8,579,964 to Lane et. al., the entire contents of which are incorporated by reference herein.

Generally, delivery handle assembly 4 includes a distal actuator such as a thumbwheel 11 and a proximal actuator such as a thumbwheel 12, both of which are integrally associated with the delivery handle assembly 4, which is comprised of an A-side delivery handle housing 22, and a B-side delivery handle housing 23. Distal thumbwheel 11 and proximal thumbwheel 12 are also rotatably positionable with respect to the delivery handle assembly 4, serving as actuators by way of internal threads (not shown) and enabling translational control of various catheters within the delivery catheter assembly 7, further evidence of which will be detailed in a later section. The delivery handle assembly 4 is operatively coupled to the valve capsule assembly 8 via the delivery catheter assembly 7, which functions in one aspect as a motion translation agent. In some embodiments, the delivery handle assembly 4, delivery catheter assembly 7 and valve capsule assembly 8 can form a delivery system 26. In some embodiments, the steering handle 5 and steerable catheter assembly 7 can form a steering guide 10, which provides a path through which the delivery system 26 can translate and rotate, and from which it may take its shape in order to traverse tortuous vasculature during implantation. Taken altogether, the delivery system 26 and steering guide 10 can form the trans-septal delivery system 1.

Figure 17A:
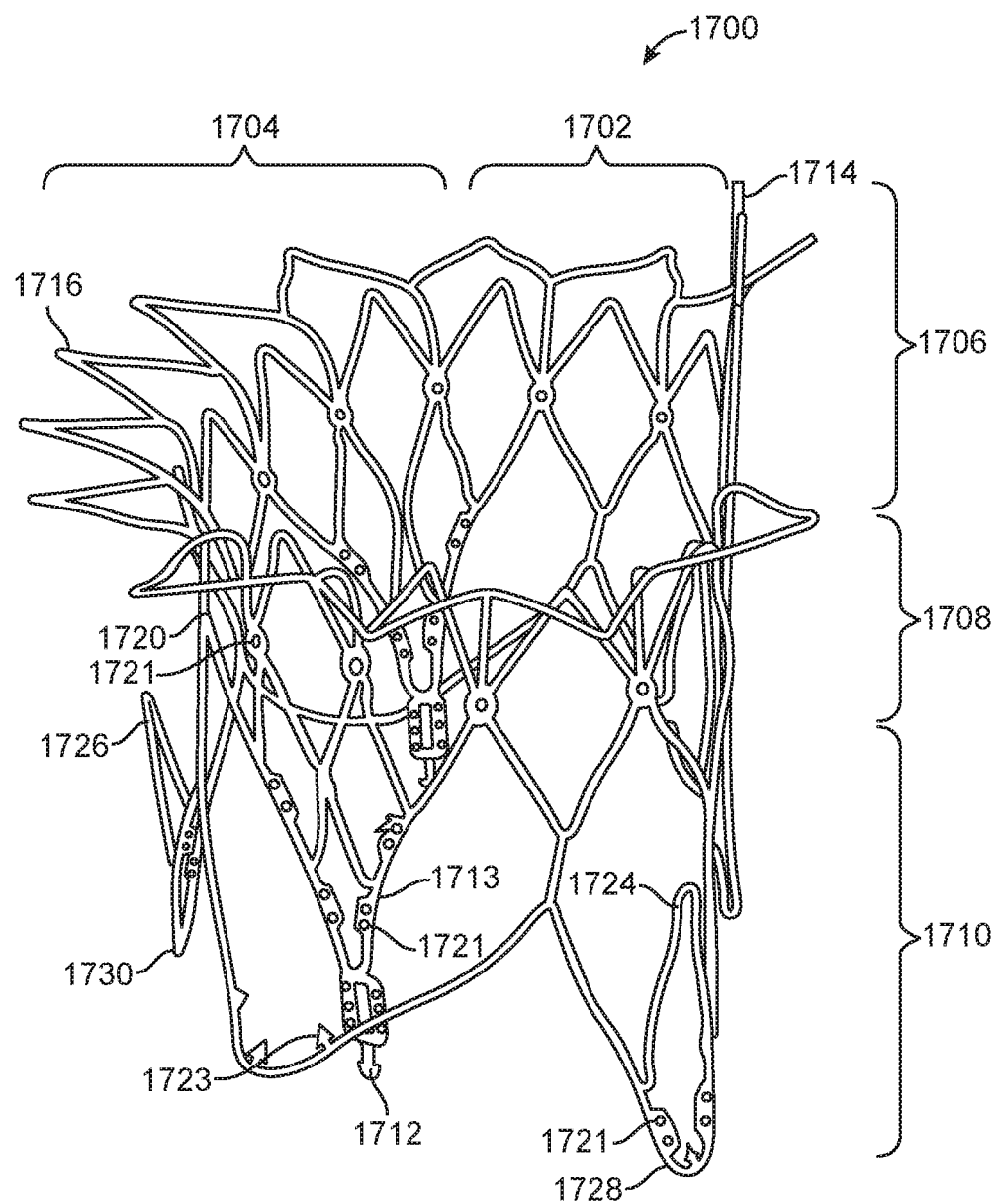
FIG. 17A is a perspective view of a prosthetic mitral valve.
Figure 17B:
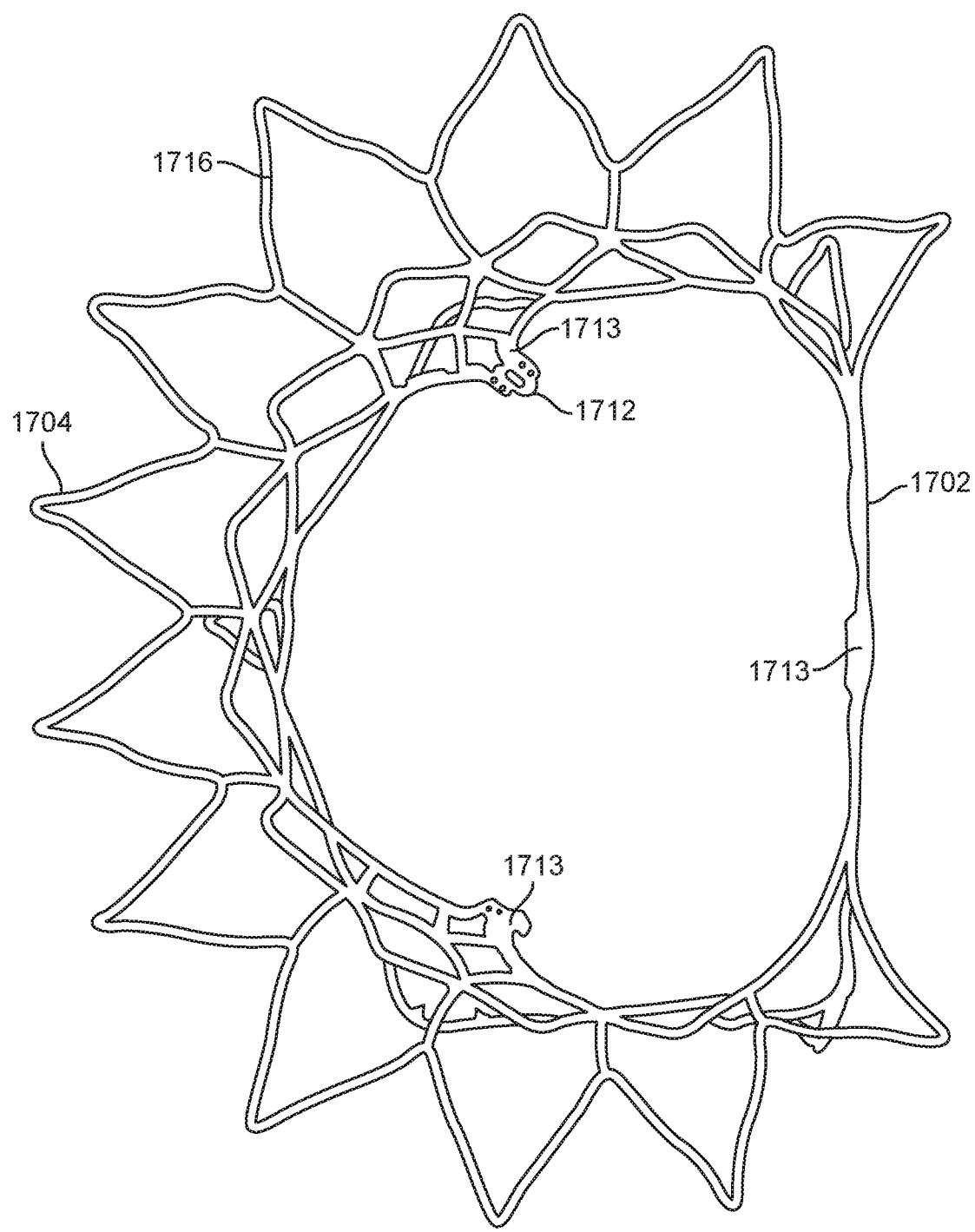
FIG. 17B is a top view of the prosthetic valve in FIG. 17A.
Figure 18A:
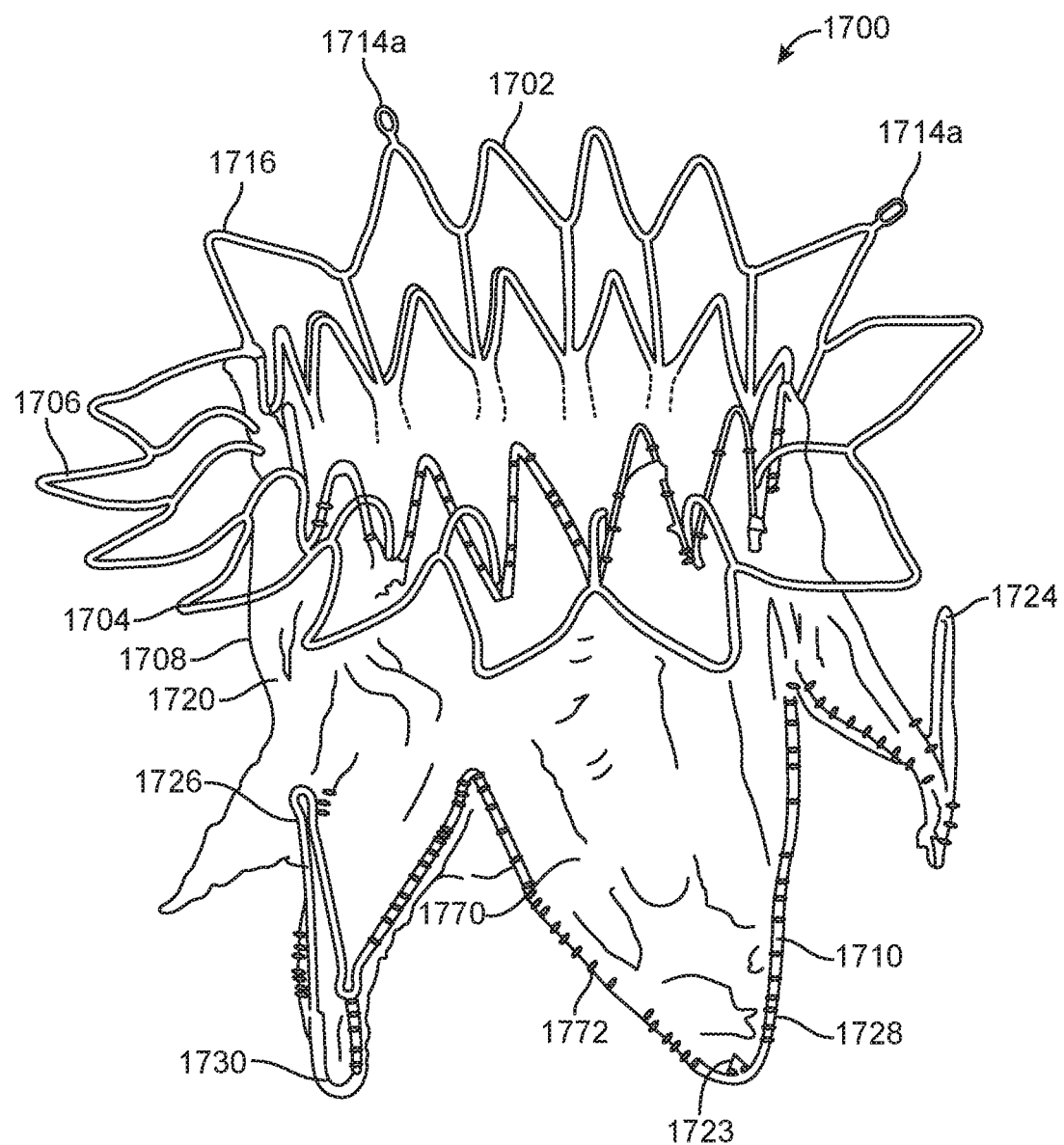
FIG. 18A illustrates a perspective view of the prosthetic valve in FIG. 17A.

Valve capsule assembly 8 may exhibit various constructions. For example, the distal capsule 14 and proximal capsule 13 may be formed from substantially rigid, stainless steel, polymer, metal or otherwise rigid tubing, from collapsible, flexible tubing, or from shape-settable exotic metal alloys which exhibit shape memory characteristics and are actuated by temperature gradients inherent to the human physiology, such as nitinol. Presently, portions of the valve capsule assembly 8 can be translatably controlled by the turning of either the distal thumbwheel 11, or the proximal thumbwheel 12, located in the delivery handle assembly 4. By rotating the distal thumbwheel 11, the proximal capsule 14 can be translatably positioned along the axis of the capsule assembly 8 in order to reveal certain portions of the prosthesis such as a prosthetic mitral valve for example, as shown in FIGS. 17A-17B and 18A-A8B, that is entrained within. By rotating the proximal thumbwheel 12, the proximal capsule 13 can be translatably positioned along the axis of the valve capsule assembly 8, again preferably revealing and releasing certain portions of the prosthetic valve (not shown). Capsule variations will be described in detail in a later section.

Figure 7:
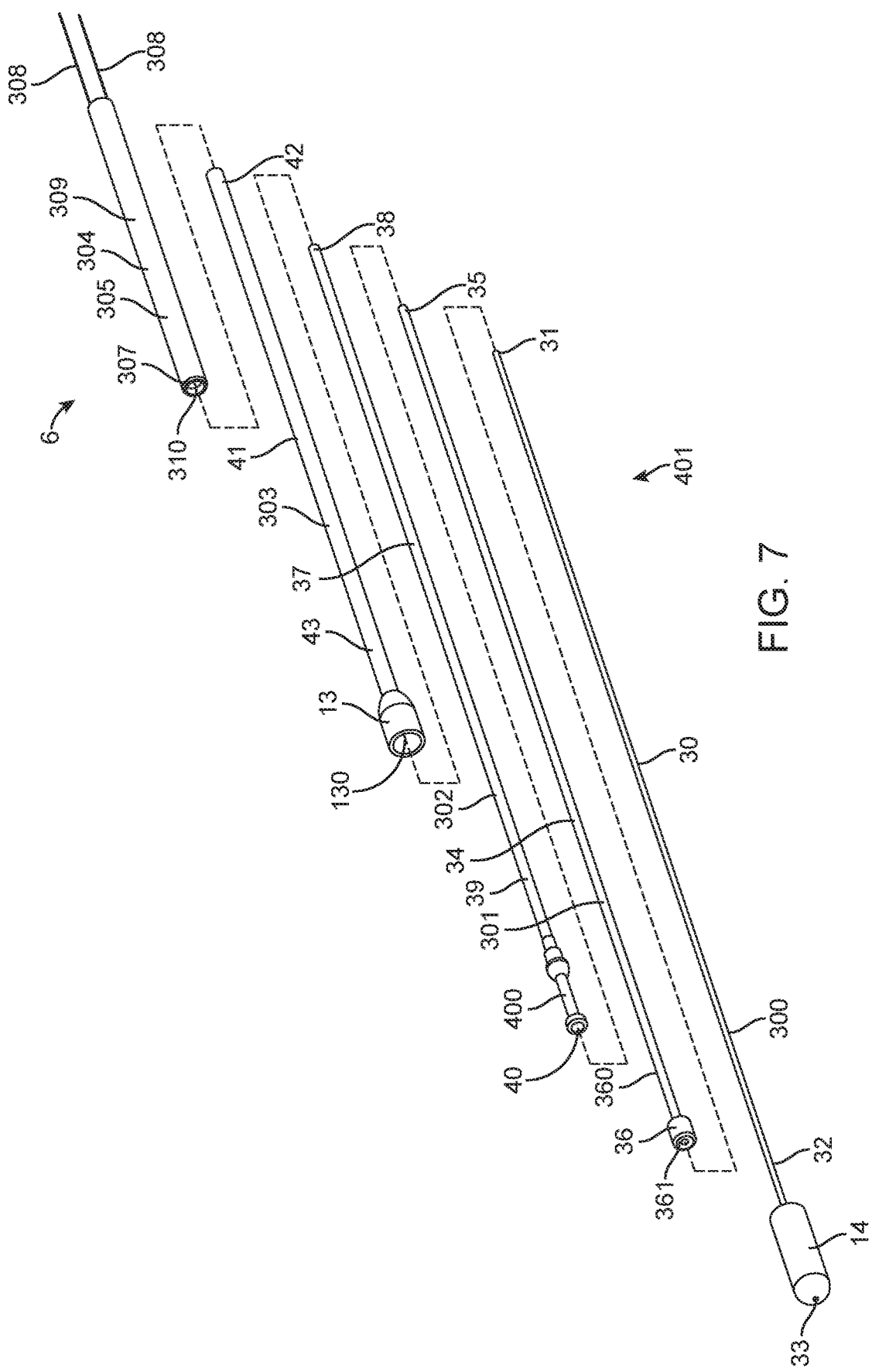
FIG. 7 is an assembly view of the delivery catheter portion of the delivery system seen in FIG. 1.

With reference to FIG. 7, the delivery catheter assembly 7 is generally comprised of a family of nested catheters concentrically and slidably disposed over one another. The innermost catheter in the family of nested catheters is the guidewire catheter 30 which has a distal section 32 that is coupled to the distal capsule 14, and a proximal section 31, with a guidewire lumen 33 that is generally sized to accept a guidewire running therebetween. The guidewire catheter 30 has a constant outer diameter and a constant inner diameter throughout its entire length, as well as a flexible section 300 which allows for articulation. The guidewire catheter 30 is generally configured to be able to fit inside of and translate slidably with respect to the bell catheter 34. The bell catheter 34 has a distal section 360 that is coupled to a bell 36, wherein the bell can be generally cylindrically shaped having a diameter larger than the bell catheter, and a proximal section 35, with an inner lumen 361 that is generally sized to accept the guidewire catheter 30 running therebetween. The bell catheter 34 has a constant outer diameter and a constant inner diameter throughout its entire length, as well as a flexible section 301 which allows for articulation. The bell catheter 34 is generally configured to be able to fit inside of and slidably translate with respect to the anchoring catheter 37. The anchoring catheter 37 has a distal section 39 that is coupled to an anchor 400, wherein the anchor can be generally cylindrically shaped and have a plurality of anchoring slots circumferentially positioned to receive valve commissure anchoring portions (not shown), and a proximal section 38, with an inner lumen 40 that is generally sized to accept the bell catheter 34 running therebetween. The anchoring catheter 37 has a constant outer diameter and a constant inner diameter throughout its entire length, as well as a flexible section 302 which allows for articulation. The anchoring catheter 37 is generally configured to be able to fit inside of and translate with respect to the sheath catheter 41. The sheath catheter 41 has a distal section 43 that is coupled to the proximal capsule 13, wherein the proximal capsule can have a cylindrical portion terminating in a cap portion, and wherein the cap portion can have a rounded dome-like surface, and a proximal section 42, with an inner lumen 130 that is generally sized to accept the anchoring catheter 37 running therebetween. The sheath catheter 41 has a constant outer diameter and a constant inner diameter throughout its entire length, as well as a flexible section 303 which allows for articulation. The sheath catheter 41 is generally configured to be able to fit inside of and slidably translate with respect to the steering catheter assembly 6. The steering catheter assembly 6 is comprised of a steerable catheter 309, a pull ring 307, wherein the pull ring can have a circular ring-like shape located at the distal section 305 of the catheter, a plurality of pull wires 308 located at the proximal section of the catheter, a flexible section 304 that allows for articulation, and an inner lumen 310 running throughout the entire length. For each pull wire 308 there is a corresponding lumen (not shown) that runs the entirety of the steerable catheter 309.

Generally, the steering guide 10 includes an interface section 9 that is comprised of an o-ring type interface of cylindrical shape similar to a gasket, which is embedded within A and B side steering handle housings 24 and 25 respectively, the A-side steering handle housing 24, the B-side steering handle housing 25, an actuator such as a steering thumbwheel 16, wherein the steering thumbwheel can have a generally cylindrical shape, a catheter strain relief 27, and a steerable catheter assembly 6. The steering thumbwheel can additionally include one or more protrusions separated by one or more recesses or slots to provide a surface to facilitate grasping and turning the wheel. In some embodiments, the steering thumbwheel can have a textured surface with ribs to facilitate grasping and turning the wheel. The interface section 9 provides a dynamic seal between the steering handle 5 and the delivery catheter assembly 7 thus allowing for slidably sealed catheter translation thereby; the delivery catheter assembly thus may traverse therethrough and exit towards the distal end of the steering guide 10 at the terminal, articulated end 15 of the steerable catheter assembly 6. While the interface section 9 provides a dynamic seal, the delivery catheter assembly 7 may still translate and rotate within the steering guide 10, in order to define accurate positioning within a patient, at the target implant site. Detail regarding the implant procedure and target implant site will be discussed in a later section. In order to actuate the steerable portion of the steering catheter assembly 6, the steering thumbwheel 16 must be turned. When the steering thumbwheel 16 is turned, the articulated end 15 of the steerable catheter assembly 6 will bend in the same direction as the direction of thumbwheel turning. This motion translation is achieved through the use of internal pull wires 308, as depicted for example in FIG. 7, that are distally in mated connection (such as a welded connection, or using fasteners, or adhesives, or any suitable method of fastening) with a pull ring 307, and proximally connectably communicate with the internal mechanisms which are inherent to the steering handle 5 and will be described in further detail in a later section.

Figure 2D:
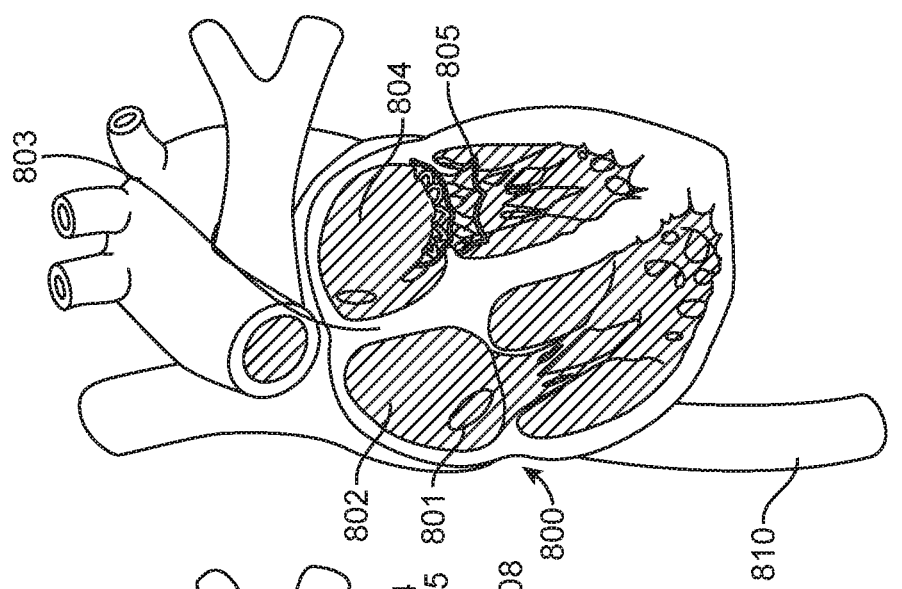
Figure 2E:
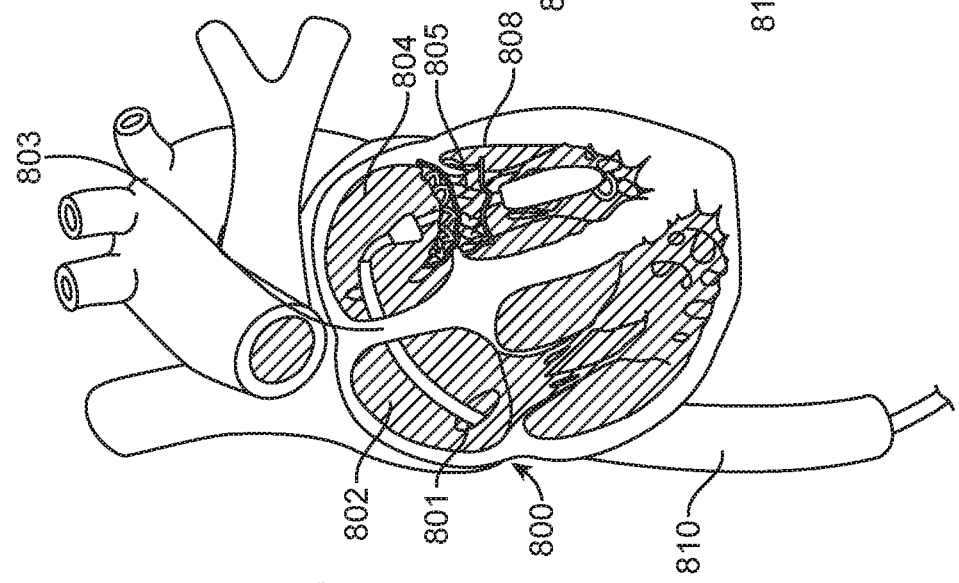
Figure 2F:
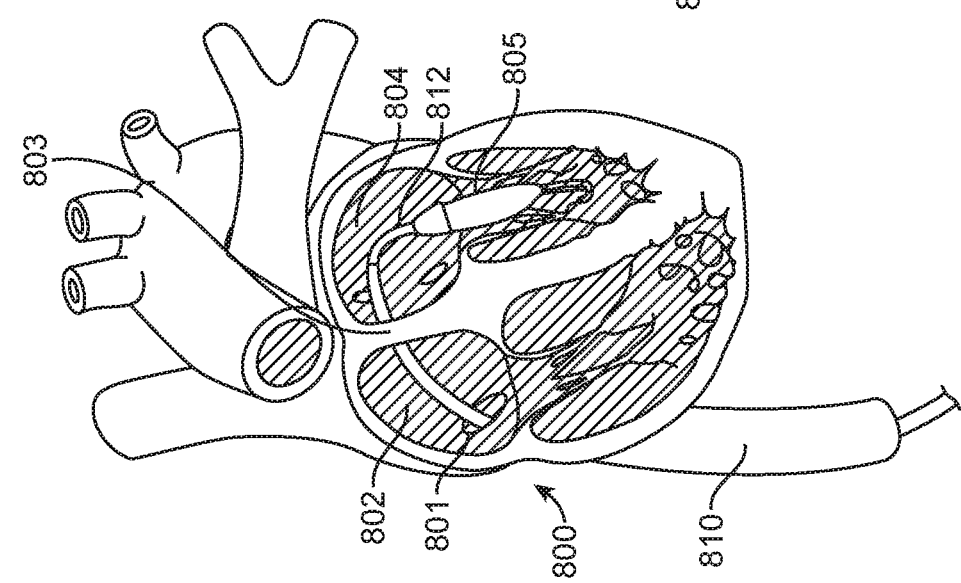

Turning now to FIGS. 2A-2F, the sequence of steps generally followed during a trans-septal valve implantation are incorporated for reference. FIG. 2A describes a general depiction of a partial view (with anterior ventricular surface, pulmonary trunk, and aorta removed) of a human heart 800. The steering guide 7 will follow a guidewire 811 that has previously been placed in order to provide a path that leads to the target implant site. During a typical procedure, the steering guide 7 will enter the inferior vena cava 810 by way of the descending inferior vena cava (not shown) and first an incision at the femoral vein near the groin (not shown). The steering guide 7 will then exit the inferior vena cava 810 through a caval foramen 801 which acts as an inlet to the right atrium 802 (FIG. 2B). Once in the right atrium 802, the steering guide 10 will then penetrate the foramen ovale 803 in the septal wall and gain access to the left atrium 804. At the left atrium 804 (FIG. 2C), the steering guide 10 will be aimed towards the mitral annulus 805 in order to provide a direct channel towards the implant site (mitral annulus 805) for the delivery catheter 812 (FIG. 2D) to operate within. Once at the target implant site (FIG. 2E), the delivery catheter 812 will operate to deploy the prosthetic valve 808. Once the valve 808 has been deployed, the delivery catheter 812 can be fully removed (FIG. 2F).

Figures 3A, 3B, 3C, 3D:
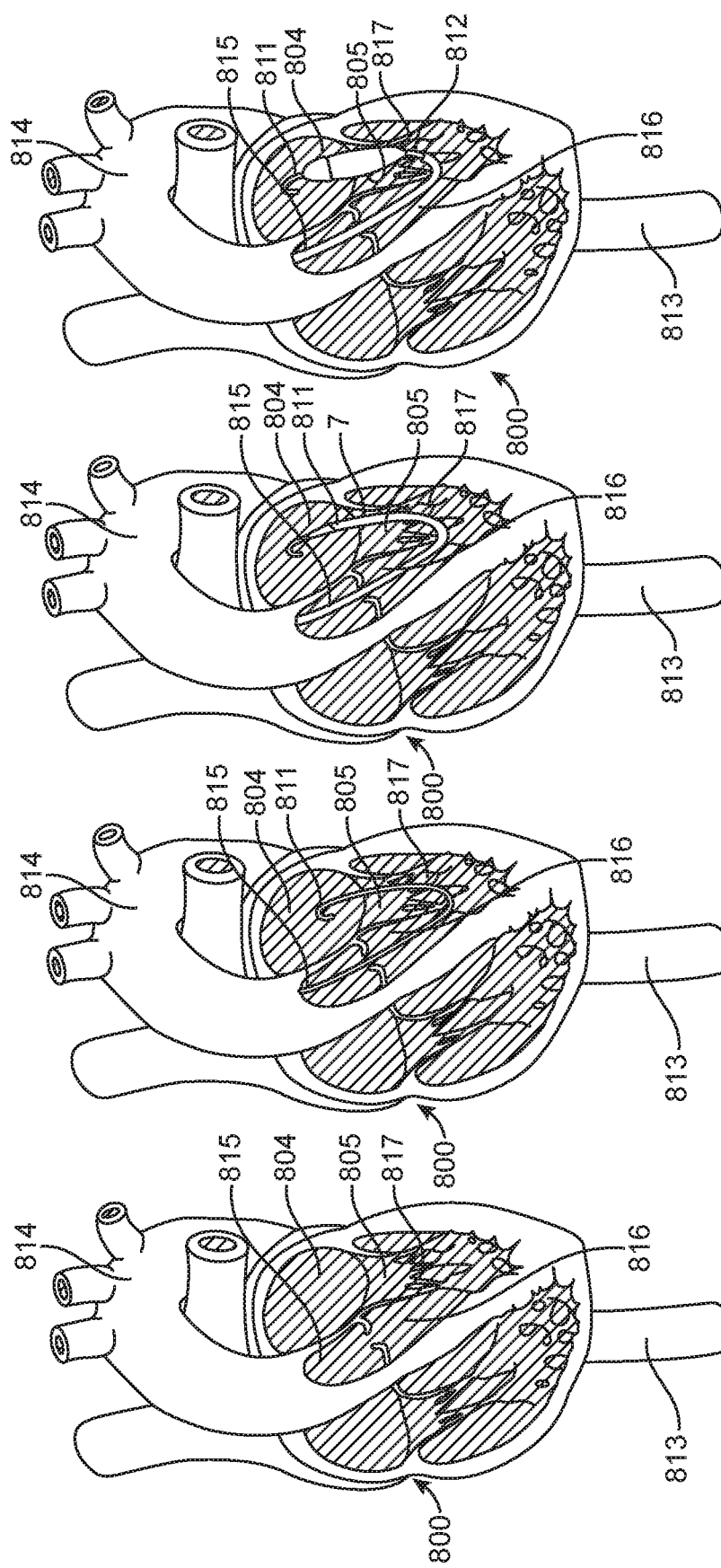
FIGS. 3A-3D are sequential views of the procedural pathway traversed by the prosthesis during a trans-aortic implantation procedure.

Again turning, now to FIGS. 3A-3D, the sequence of steps generally followed during a trans-aortic valve implantation are incorporated for reference. FIG. 3A describes a general depiction of a partial view (with anterior ventricular surface, pulmonary trunk, and aortic root surface removed) of a human heart 800. The steering guide 7 will again follow a guidewire 811 that has previously been placed in order to provide a path that leads to the target implant site. During a typical procedure, the steering guide 7 will enter the descending aorta 813 by way of an incision at the femoral artery near the groin (not shown). The steering guide 7 will then continue up the descending aorta 813 and cross the aortic arch 814 before passing through the aortic valve 815 and descending into the left ventricular outflow tract 816 (LVOT). After emerging from the LVOT 816, and entering the left ventricle 817, the steering guide 7 must then make a sharp turn and point upward and towards the mitral annulus 805. At this point, the delivery catheter 812 may be advanced within the steering guide 7 in order to approach the target implant site (mitral annulus 805). Once at the target implant site (FIG. 2E), the delivery catheter 812 will operate to deploy the prosthetic valve 808. Once the valve 808 has been deployed, the delivery catheter 812 can be fully removed (FIG. 2F).

With particular reference to FIGS. 4-7, the internal mechanisms of the trans-septal delivery system 1 that permit functionality will be described. Specifically, FIG. 4 illustrates an embodiment of an assembly of a trans-septal delivery system 1 shown in exploded view. The trans-septal delivery system 1 is displayed in sections in order to make description of the internal parts more easily understood. Delivery handle section 403 will be described in further detail below with reference to FIG. 5. Steering handle section 402 will be described in further detail below with reference to FIG. 6. Finally, delivery catheter section 401 has previously been described above with reference to FIG. 7.

Figure 5:
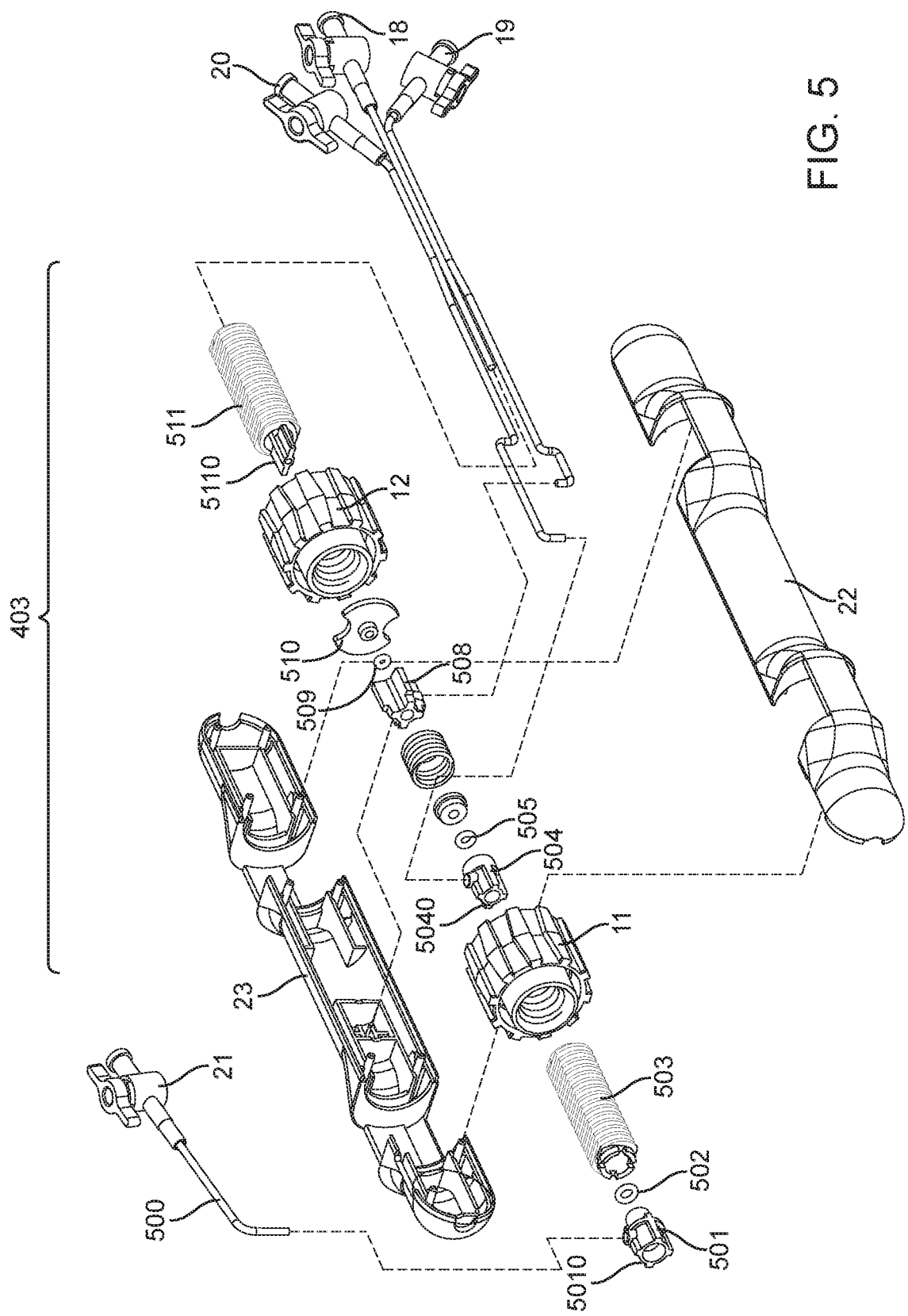
FIG. 5 is an assembly view of the delivery handle portion of the delivery system seen in FIG. 1.

Referring now to FIG. 5, the delivery handle section 403 is generally comprised of an A-side delivery handle housing 22 that is in mating connection with a B-side delivery handle housing 23, actuators such as a plurality of thumbwheels (distal thumbwheel 11 and proximal thumbwheel 12), a plurality of force transferring leadscrews (distal leadscrew 503 and proximal leadscrew 511) that may translate proximally or distally depending on the rotation of the thumbwheel within said plurality of thumbwheels, a plurality of hemostatic ports and related tubing (hemo port A 21, hemo port B 20, hemo port C 18 and hemo port D 19) which provide the ability to remove entrained air boluses from concentrically nested catheters within the system, and various other components and fasteners that shall be described in further detail. Referring specifically to the motion transferring elements of the delivery handle section 403, a distal leadscrew 503 is in threaded connection with a distal thumbwheel 11 and by turning said distal thumbwheel 11, translational motion is imparted upon the distal leadscrew 503. The motion of the distal leadscrew 503 is transferred to the sheath catheter 41 by way of a connection between the proximal end 42 of the sheath catheter 41 and the distal end 5010 of the distal leadscrew cap 501, which itself is mated with adhesive (medical grade UV cure adhesive, or medical grade cyanoacrylate adhesive, or any suitable medical grade adhesive for plastics or polymers, etc.) to the distal leadscrew 503. The distal leadscrew cap 501 also permits the ejection of air by way of a sealed interface (distal o-ring 502) between the sheath catheter 41 and the anchoring catheter 37, and an outlet hemo port A 21. A stationary screw cap 504 is entrained within the A and B side handle housings 22, 23 respectively, and provides location and retention for the anchoring catheter 37, whereby the proximal end 38 of the anchoring catheter 37 is in mated connection (medical grade UV cure adhesive, or medical grade cyanoacrylate adhesive, or any suitable medical grade adhesive for plastics or polymers, or by way of fastening mechanical threads) with the distal end 5040 of the stationary screw cap 504. The stationary screw cap 504 also permits the ejection of air by way of a sealed interface (medial o-ring 505) between the anchoring catheter 37 and the bell catheter 34, and an outlet hemo port B 20. A proximal leadscrew 511 is in threaded connection with a proximal thumbwheel 12 and by turning said proximal thumbwheel 12, translational motion is imparted upon the proximal leadscrew 511. The motion of the proximal leadscrew 511 is transferred to the guidewire catheter 30 by way of a connection between the proximal end 31 of the guidewire catheter 30 and the distal end 5110 of the proximal leadscrew 511. Proximal leadscrew 511 motion is also transferred to the bell catheter 34 by way of a slidable interference between the distal end 5110 of the proximal leadscrew 511 and the proximal leadscrew plate 510, whereby the proximal leadscrew plate 510 is in mated connection with the proximal leadscrew cap 508, and the proximal leadscrew cap 508 houses the proximal end 35 of the bell catheter 34. The proximal leadscrew cap 508 also permits the ejection of air by way of a sealed interface (proximal o-ring 509) between the bell catheter 34 and the guidewire catheter 30, and an outlet hemo port C 19. The proximal leadscrew 511 permits the ejection of air by way of an outlet hemo port D 18 which is in mated connection with the proximal leadscrew 511.

Figure 6:
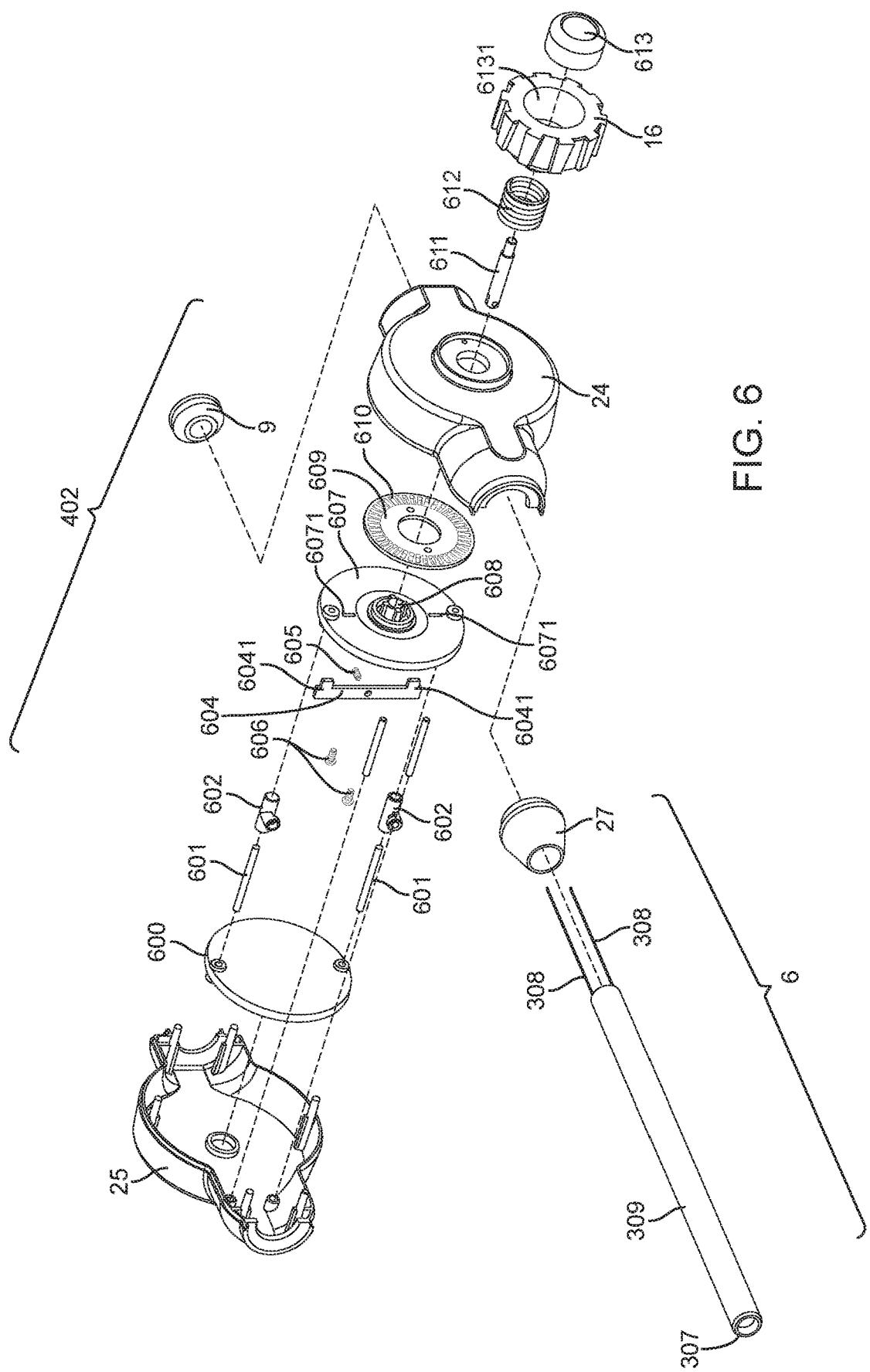
FIG. 6 is an assembly view of the steering guide portion of the delivery system seen in FIG. 1.

Referring now to FIG. 6, the steering handle section 402 is generally comprised of an A-side steering handle housing 24 that is in mating connection with a B-side steering handle housing 25, a steerable catheter assembly 6 that is in mating connection with a catheter strain relief 27, an interface 9, a plurality of rotatable disks (B-side rotatable disk 600 and A-side rotatable disk 607), a steering thumbwheel 16, a push button 613, and various other components and fasteners that shall be described in further detail. Referring specifically to the steering elements of the steering handle section 402, a steering thumbwheel 16 is in mating connection with a locking hub 608 that is centered within the A-side rotatable disk 607. The A-side rotatable disk 607 and B-side rotatable disk 600 are coupled together by way of a plurality of carrier rods 601, and work mechanically to spin within the handle housing that is comprised of the A-side steering handle housing 24 and B-side steering handle housing 25. Since the A-side rotatable disk 607 is connected to the steering thumbwheel 16, rotation of the steering thumbwheel 16 causes rotation of the A-side rotatable disk 607. A specific function of the plurality of rotatable disks (B-side rotatable disk 600 and A-side rotatable disk 607) is to actuate the plurality of pull wires 308 by way of tensioning hinges 602 that may spin freely on the carrier rods 601 and that are also connected to the pull wires 308 and also apply tension to them when turned. Referring now specifically to the locking elements of the steering handle section 402, a push button 613 is in threaded connection with a push button pin 611 that acts as a shaft. The push button 613 is located within a cavity 6131 that allows for direct translation when the button is depressed. A push button spring 612 is housed between the inside surface of the push button 613, and the bottom of the cavity 6131 and provides return force for when the depressed push button 613 is released. Motion from the push button 613 is transferred along the push button pin 611 directly to a cross bar 604 that is fastened to the push button pin 611 by way of a setscrew 605. When the push button pin 611 translates as the push button 613 is depressed, the cross bar 604 also translates and a plurality of cross bar pegs 6041 that are located on the ends of the cross bar 604 thus translate as well. When in an un-depressed state, the cross bar pegs 6041 are seated within a plurality of slots 6071 that appear on the periphery of the A-side rotatable disk 607. The cross bar pegs 6041 then also project through the slots 6071 and may rest within any of the circumferential slits 610 that appear in an array about the periphery of a position disk 609 that is mounted to the inside surface of the A-side steering handle housing 24 by threaded fasteners 606. When in a depressed state, the cross bar pegs 6041 are moved away from the circumferential slits 610 until clearance is achieved, and the locking mechanism enables free rotation of the cross bar 604, as well as all aspects that are directly connected to the A-side rotatable disk 607. Further detail regarding the mechanics behind the locking mechanism can be seen in FIG. 9, which is incorporated herein for reference.

By way of cross-sectional illustration, FIGS. 8A-8D show specific internal features of the devices described herein, and will now be relied upon to reveal further detail. FIG. 8A depicts the entire trans-septal delivery system 1 comprised of a distal end 3, a steerable catheter assembly 6, a steering handle 5, and a delivery handle assembly 4 therebetween the distal end 3 and the proximal end 2. At the distal end 3 of the trans-septal delivery system 1 is located the distal 14 and proximal 13 capsules, which entrain a prosthetic valve therein. An articulated end 15 of the steerable catheter assembly 6 is in mating connection with the distal-most portion of the steering handle 5, which locates and controls it thereby. The steering thumbwheel 16 provides actuation control of the articulated end 15 of the steerable catheter assembly 6. Continuing proximally, the delivery handle assembly 4 is depicted, which houses the distal 11 and proximal 12 thumbwheels, each being responsible for the translation of the proximal 13 and distal 14 capsules, respectively. A hemo port A 21 is provided and housed by the a-side delivery handle housing 22 and b-side delivery handle housing 23 (not shown). Further hemo ports B, C, and D (20, 19, and 18 respectively) are also provided, the functions of which being described in greater detail in previous sections.

FIG. 8B introduces a cross-sectional view AA of the aforementioned depiction in FIG. 8A, which reveals the internal mechanisms of the distal end 3, the steering handle 5, and the delivery handle assembly 4. Cross-section AA of FIG. 8B shows the internal surfaces of the distal capsule 14, and the proximal capsule 13, as well as the articulated end 15 of the steerable catheter assembly 6, all of whose mechanical interactions have been described previously above. Also depicted is an internal view of the steering handle 5, and the delivery handle assembly 4 which displays the elements distal 11 and proximal 12 thumbwheels, and a-side delivery handle housing 22. A detail section C 250 is provided, whereby the enlarged illustration of the contents of detail section C 250 appear in FIG. 8C.

As mentioned, FIG. 8C is the enlarged illustration of the contents of detail section C 250 of FIG. 8B, and further detail of the internal features of the valve capsule assembly 8 are hereby provided. It can be seen that the distal capsule 14 is internally threaded at a threaded portion 460, which provides mating means for a guidewire catheter threaded insert 490 that is embedded near the distal end 32 of the guidewire catheter 30. Similarly, the bell 36 is internally threaded at a threaded portion 470, which provides mating means for a bell catheter threaded insert 500 that is embedded near the distal end 360 of the bell catheter 34. Similarly, the anchor 400 is internally threaded at a threaded portion 480, which provides mating means for an anchoring catheter threaded insert 510 that is embedded near the distal end 39 of the anchoring catheter 37. Further regarding the bell 36, it can be seen that the bell 36 is shown in position and concentrically oriented to the distal most portion 450 of the anchor 400, over which it may translate when actuated accordingly by the delivery handle assembly 4 (not shown). It should be apparent that the connected pair that is comprised of the distal capsule 14 and guidewire catheter 30 may move in tandem concentrically within the similarly connected pair that is comprised of the bell 36 and bell catheter 34, which may also move in tandem concentrically within the similarly connected pair that is comprised of the anchor 400 and anchoring catheter 37 which are stationary, but inherently flexible by virtue of their construction. The proximal capsule 13 by way of attachment to the sheath catheter 41 also form a connected pair that may move in tandem concentrically over the previously discussed catheters.

FIG. 8D depicts the result of the cross-section B-B introduced in FIG. 8A. As previously described, a plurality of handle housings, A-side 24 and B-side 25 are in mated connection and form the entirety of the housing which comprises the steering handle 5. Within this cross-section B-B of FIG. 8D can also be seen a plurality of carrier rods 601 that matingly pin together the A-side 607 and B-side 600 rotatable disks. Also shown are the cross bar 604, push-button pin 611, and setscrew 605 that fasten said bar and said pin together in mating connection. The steering thumbwheel 16, which houses the push button 613 and by extension the push button spring 612 is further revealed, additionally.

Figure 9A:
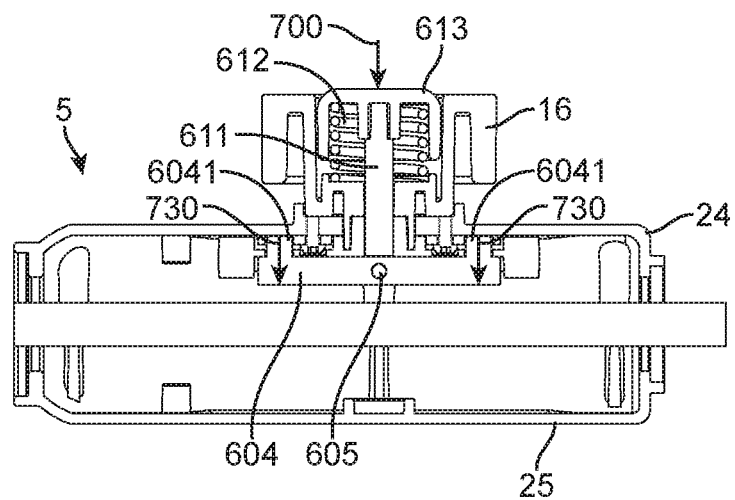
FIGS. 9A-9C are cross-sectional views of the steering handle portion taken along the line A-A in FIG. 8A.
Figure 9B:
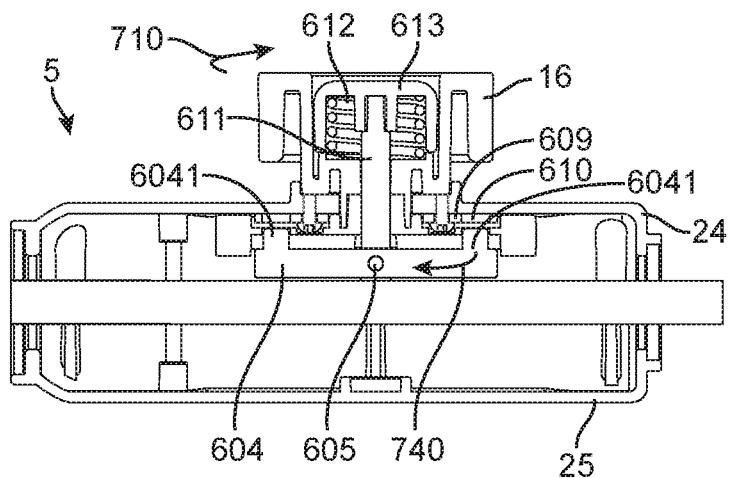
Figure 9C:
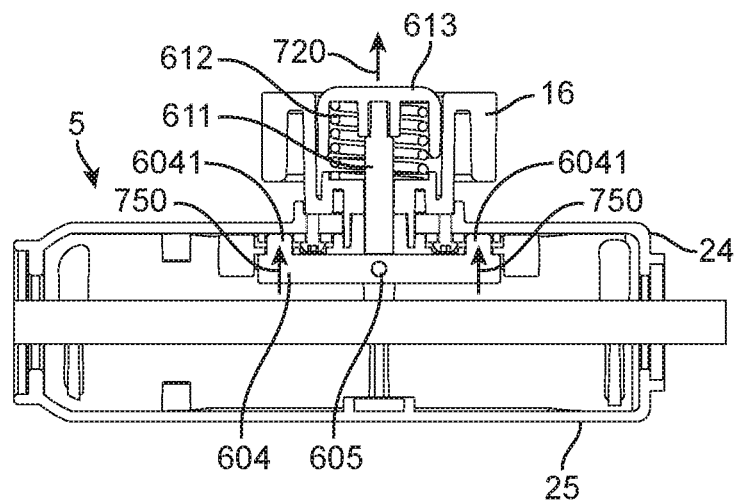

FIGS. 9A-9C illustrate the internal mechanics of the locking mechanism that is inherent to the steering handle 5 (of which these figures provide a cross-sectional view), and further illustrate the dynamic relationships between the components, and the manner in which they may be operated. Beginning with FIG. 9A, the sequence of operation that comprises pushing a button, turning a knob, and then releasing the button while maintaining an achieved angular position by the button is set forth. Specifically, FIG. 9A depicts the depression (arrow indicating translation 700) of the push button 613 that is mounted within the steering thumbwheel 16 and biased internally by the opposing force of the push button spring 612. As the push button 613 is matingly connected to the cross bar 604 by way of the push button pin 611 and the setscrew 605, when the push button 613 is translated through depression, the cross bar 604 is also translated (arrows indicating translation 730) in the same direction as the push button 613. Once the cross bar 604 is fully translated, a plurality of cross bar pegs 6041 described on the ends of the cross bar 604 become disengaged from circumferential slits 610 (FIG. 9B) that are provided by the position disk 609 (FIG. 9B).

Continuing within FIG. 9B, once the cross bar 604 is unconstrained it is thus free to rotate (arrows indicating rotation 740) by the application of a torque to the steering thumbwheel 16 (arrows indicating rotation 710).

FIG. 9C provides the final step in the operation of the push button 613 mechanism of the steering thumbwheel 16 for steering and positional lockout. After the appropriate rotational position is achieved with the steering thumbwheel 16, the push button 613 is released. This allows for translation in the opposite direction (arrows indicating translation 720) to that experienced when the push button 613 is depressed, due to the biasing force of the push button spring 612. Releasing the push button 613 also allows the cross bar 604 to translate (arrows indicating translation 750) and by extension, the cross bar pegs 6041 may thus achieve re-engagement with the circumferential slits 610 (FIG. 9B) and provide lockout against further rotation of the steering thumbwheel 16 and by extension disruption of position of the steerable catheter 309 (not shown).

Turning now to FIGS. 10A-10D, a sequence of images is provided which depict the rotation of the steering thumbwheel 16 and the ensuing effect at the valve capsule end of the system. Beginning with FIG. 10A, when a torque is applied to the steering thumbwheel 16, rotational motion is transferred to the A-side rotatable disk 607, which is in communication with a plurality of pull wires 308 that are further internally embedded at the articulated end 15 of the steerable catheter assembly 6. The pull wires act to preferentially pull the articulated end 15 of the steerable catheter assembly 6 in the direction of steering thumbwheel 16 rotation. Further application of torque (FIG. 10B-10D) results in a further rotation of the steering thumbwheel 16 and yet further bending of the articulated end 15 of the steerable catheter assembly 6.

Now with specific reference to FIGS. 11A-11D, a particular embodiment of a valve capsule assembly 8, and general deployment sequence of a trans-catheter valve prosthesis are herein illustrated. Details regarding the trans-catheter valve prosthetic referenced herein are described in commonly-owned U.S. Pat. No. 8,579,964 to Lane et. al. As depicted in FIG. 11B, a trans-catheter valve prosthesis 1100 is entrained within the valve capsule assembly 8, after having been preferentially crimped (details regarding the loading device used to crimp said trans-catheter valve prosthetic are described in commonly-owned U.S. Pat. Publication. No. 20/0155990, the entire contents of which are incorporated herein by reference, and loaded therein. The valve capsule assembly 8 can comprise a generally cylindrical structure having a proximal end and a distal end, wherein each of the proximal and distal ends terminates in a rounded dome-like surface. As shown in FIG. 1, the valve capsule assembly can comprise a proximal capsule 13 and a distal capsule 14, wherein the proximal capsule 13 is disposed at a proximal end of the valve capsule assembly, and the distal capsule 14 is disposed at a distal end of the valve capsule assembly. Each of the proximal capsule 13 and the distal capsule 14 can have a cylindrical portion with one end of the cylindrical portion having an open circular shape and the other end having a cap portion that can have a rounded dome-like surface. As shown in FIG. 3, the open circular shape of proximal capsule 13 can be configured to meet with or abut against the open circular shape of distal capsule 14, with the cap portion of the proximal capsule forming the proximal end of the valve capsule assembly, and the cap portion of the distal capsule forming the distal end of the valve capsule assembly.

FIG. 11C illustrates the valve 1100 in staged deployment after the proximal capsule 13 has been translated away from the valve 1100, and the atrial skirt 1101 has been revealed and allowed to self-expand. FIG. 11D illustrates the valve 1100 with the atrial skirt 1101 fully expanded, after the distal capsule 14 has been translated away from the valve 1100. A plurality of trigonal anchoring tabs 1102 have also been revealed by the movement of the distal capsule 14. FIG. 11E illustrates final deployment of the valve 1100, whereby the distal capsule 14 has translated to its maximum displacement, and the bell 36 on the bell catheter 34 has also translated maximally in order to release anchoring features of the valve (not shown) until finally full release of the valve from the delivery device has been achieved, and the valve 1100 is no longer anchored to any part of the valve capsule assembly 8.

With particular reference to FIGS. 12A-12D, an alternative embodiment of a valve capsule assembly 1205 is herein illustrated. FIG. 12A depicts a valve capsule assembly 1205 which can be comprised of a proximal capsule 13, a distal capsule sleeve 1200, and an optional balloon tip 1201 or a tapered tip. The balloon tip 1201 may be preferentially inflated or deflated in order to optimize space constraints that are inherent to the anatomical limitations found within the left ventricle of the human heart, whereby deflating the balloon tip 1201 allows the distal capsule sleeve 1200 (which is generally configured to be shorter in overall length than the previously described proximal capsule 14, FIG. 1) to translate over the balloon tip 1201 in order to enable typical deployment.

Figure 13D:
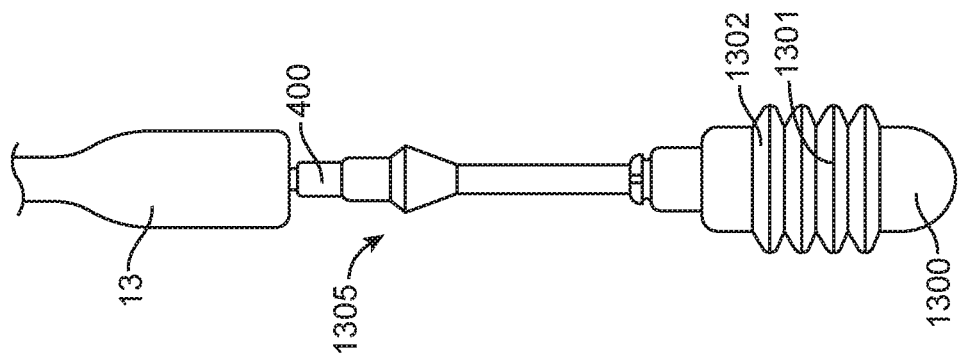
FIGS. 13A-13D are sequential partial views of an alternative embodiment of the valve capsule portion of the delivery system of FIG. 1.
Figure 13C:
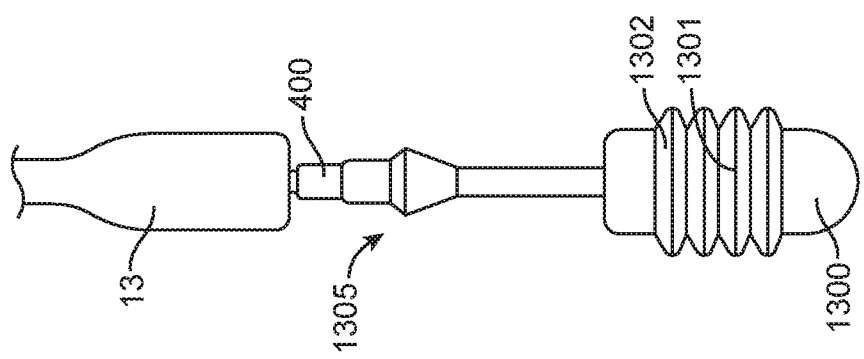
Figure 13B:
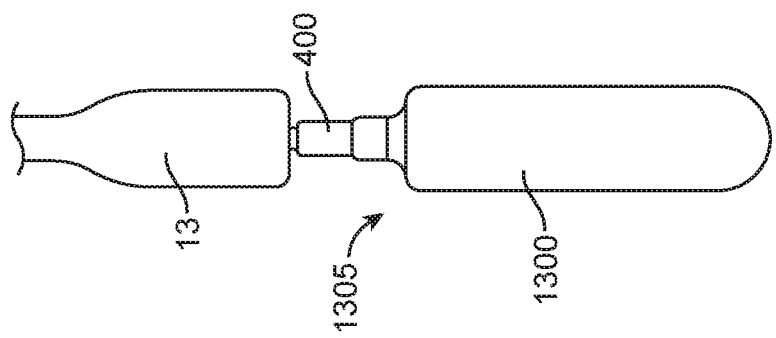
Figure 13A:
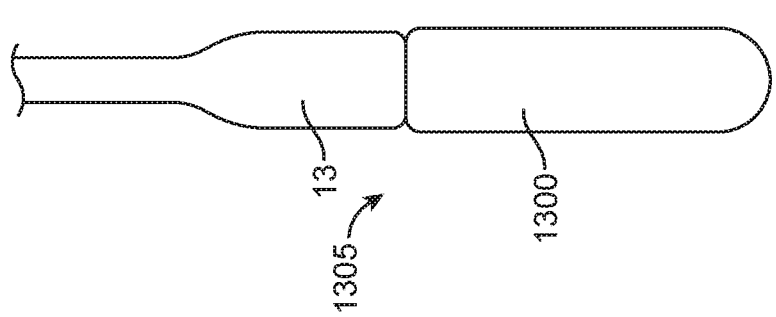

With particular reference to FIGS. 13A-13D, an alternative embodiment of a valve capsule assembly 1305 is herein illustrated. FIG. 13A depicts a valve capsule assembly 1305 which is comprised of a proximal capsule 13, and a collapsible distal capsule 1300. The collapsible distal capsule 1300 generally translates and functions in the manner of an accordion, in order to optimize space constraints that are inherent to the anatomical limitations found within the left ventricle of the human heart, whereby collapsing the distal capsule 1300 to enable typical deployment requires moving the body of the capsule into the left ventricle a shorter distance than that anticipated by the previously described proximal capsule 14 (FIG. 1). The operational function of the collapsible distal capsule 1300 relies on the actuation of a plurality of stacked rings 1301 or stackable elements that can be joined in series and can generally covered by a shroud 1302 that may be comprised of fabrics, polymers, metallic alloys or any combination thereof.

Figure 14D:
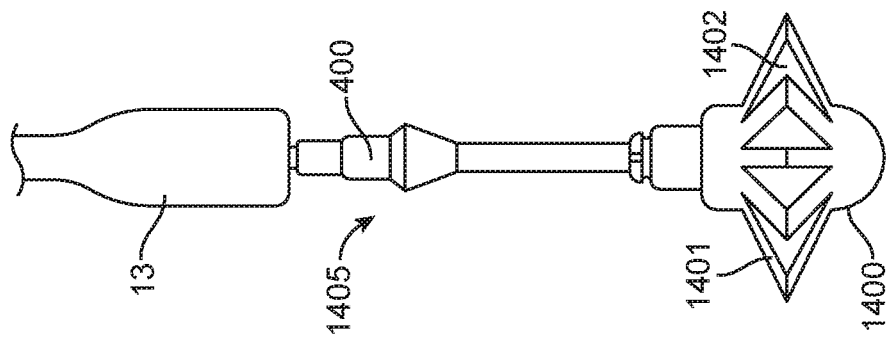
FIGS. 14A-14D are sequential partial views of an alternative embodiment of the valve capsule portion of the delivery system of FIG. 1.
Figure 14C:
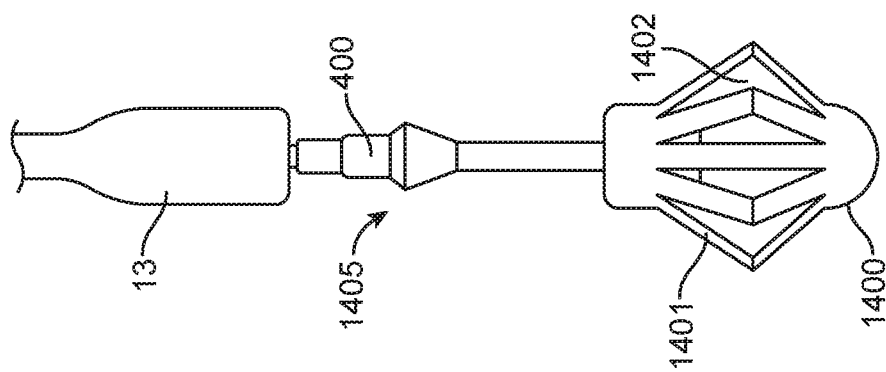
Figure 14B:
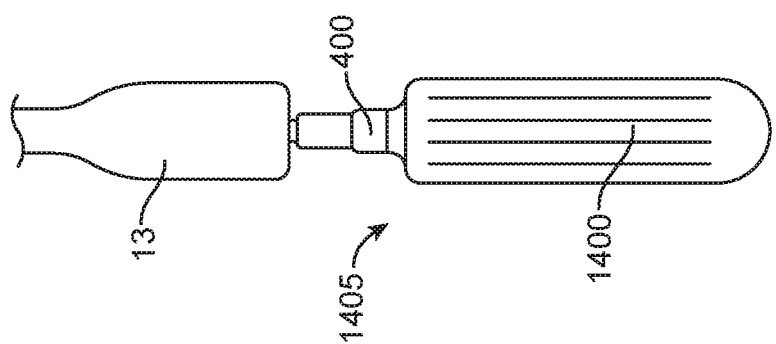
Figure 14A:
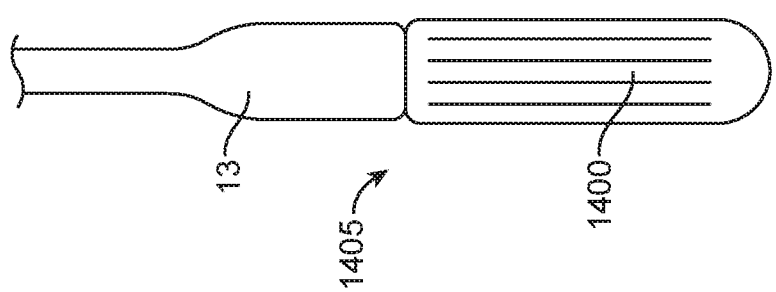

Any embodiment of a valve capsule assembly may be used in any delivery catheter as described herein. With particular reference to FIGS. 14A-14D, an alternative embodiment of a valve capsule assembly 1405 is herein illustrated. FIG. 14A depicts a valve capsule assembly 1405 which is comprised of a proximal capsule 13, and a collapsibly splined distal capsule 1400. The collapsibly splined distal capsule 1400 generally translates and functions in the manner of an umbrella, in order to optimize space constraints that are inherent to the anatomical limitations found within the left ventricle of the human heart, whereby collapsing the splined distal capsule 1400 to enable typical deployment requires moving the body of the capsule into the left ventricle a shorter distance than that anticipated by the previously described proximal capsule 14 (FIG. 1). The operational function of the collapsibly splined distal capsule 1400 relies on the actuation of plurality of hinged splines 1401 that are joined in parallel and generally covered by a shroud 1402 that may be comprised of fabrics, polymers, metallic alloys or any combination thereof. The splines 1401 can be arm-like parallel structures formed by a series of parallel cuts or incisions along a longitudinal surface of the cylindrical portion of the capsule, wherein the hinges of the splines allow each arm-like structure to bend, thus compressing or collapsing the distal capsule.

With particular reference to FIGS. 15A-15D, an alternative embodiment of a valve capsule assembly 1505 is herein illustrated. FIG. 15A depicts a valve capsule assembly 1505 which is comprised of a proximal capsule 13, and a collapsibly wired distal capsule 1500. The collapsibly wired distal capsule 1500 generally translates and functions in the manner of a flag pole (relying on the push/pull of the rigid plurality of wires 1502) in order to optimize space constraints that are inherent to the anatomical limitations found within the left ventricle of the human heart, whereby collapsing the wired distal capsule 1500 to enable typical deployment requires moving the body of the capsule into the left ventricle a shorter distance than that anticipated by the previously described proximal capsule 14 (FIG. 1). The operational function of the collapsibly wired distal capsule 1500 relies on the actuation of plurality of nitinol or similar alloy wires 1502 that are joined in parallel and proximally fastened to a structural ring 1501 and generally covered by a shroud 1504 that may be comprised of fabrics, polymers, metallic alloys or any combination thereof. Distally, the plurality of nitinol wires 1502 may be withdrawn into a plurality of distal slots 1506, and then finally a distal lumen 1507 (not shown) that resides inside of a distal cap 1503 in order to cinch the capsule in its entirety, and translate it away from the distal portion of the valve. In one particular embodiment, the distal lumen 1507 (not shown) would comprise an additional lumen (not shown) appearing within the guidewire catheter (30, FIG. 7) the additional lumen (not shown) traversing the entire delivery system and exiting through the delivery system A and B side handle halves 22, 23 respectively. The plurality of nitinol wires 1502 would traverse and exit the additional lumen (not shown), and be graspable and pullable for deployment, by an operator.

With particular reference to FIGS. 16A-16D, an alternative embodiment of a valve capsule assembly 1605 is herein illustrated. FIG. 16A depicts a valve capsule assembly 1605 which is comprised of a proximal capsule 13, and a shape memory distal capsule 1600. The shape memory distal capsule 1600 generally translates and functions in the manner of an accordion, in order to optimize space constraints that are inherent to the anatomical limitations found within the left ventricle of the human heart, whereby collapsing the shape memory distal capsule 1600 to enable typical deployment requires moving the body of the capsule into the left ventricle a shorter distance than that anticipated by the previously described proximal capsule 14 (FIG. 1). The operational function of the shape memory distal capsule 1600 relies on the actuation and stiffening of a stent-like nitinol or similar alloy frame 1600 by the temperature gradient within a patient's blood stream, that is further anchored to a structural cap 1601 and generally covered by a shroud 1601 that may be comprised of fabrics, polymers, metallic alloys or any combination thereof. A plurality of internal biasing wires 1603 enable the shape memory distal capsule 1600 to be collapsed when they are in tension, and to be extended when they are not in tension.

Prosthesis

FIG. 17A illustrates a perspective view of a preferred embodiment of a prosthetic mitral valve with optional coverings removed to allow visibility of the anchor struts. FIG. 17B illustrates a top view of the prosthetic valve in FIG. 17A from the atrium looking down into the ventricle. The valve 1700 includes an asymmetrical expanded anchor portion having a D-shaped cross-section. As shown, the anchor portion generally comprises anterior 1702 and posterior 1704 aspects along the longitudinal axis thereof, as well as atrial 1706, annular 1708 and ventricular 1710 regions. Commissures (also referred to herein as commissure posts) 1713 are also shown. The prosthetic valve 1700 has a collapsed configuration and an expanded configuration. The collapsed configuration is adapted to loading on a shaft such as a delivery catheter for transluminal delivery to the heart, or on a shaft for transapical delivery through the heart wall. The radially expanded configuration is adapted to anchor the valve to the patient's native heart adjacent the damaged valve. In order to allow the valve to expand from the collapsed configuration to the expanded configuration, the anchor portion of the valve may be fabricated from a self-expanding material such as a nickel titanium alloy like nitinol, or it may also be made from spring temper stainless steel, or a resilient polymer. In still other embodiments, the anchor may be expandable with an expandable member such as a balloon. In preferred embodiments, the anchor is fabricated by laser cutting, electrical discharge machining (EDM), or photochemically etching a tube. The anchor may also be fabricated by photochemically etching a flat sheet of material which is then rolled up with the opposing ends welded together.

The atrial skirt portion 1716 forms a flanged region that helps to anchor the prosthetic valve to the atrium, above the mitral valve. The atrial skirt includes a plurality of triangular fingers which extend radially outward from the anchor to form the flange. The posterior 1704 portion of the atrial skirt 1716 is generally round or circular, while a portion of the anterior 1702 part of the atrial skirt 1716 is flat. Thus, the atrial skirt region preferably has a D-shaped cross-section. This allows the prosthetic valve to conform to the patient's cardiac anatomy without obstructing other portions of the heart, as will be discussed below. Each triangular finger is formed from a pair of interconnected struts. The triangular fingers of the atrial skirt generally are bent radially outward from the central axis of the prosthetic valve and lie in a plane that is transverse to the valve central axis. In some embodiments, the atrial skirt lies in a plane that is substantially perpendicular to the central axis of the valve. The anterior portion 1702 of the atrial skirt 1706 optionally includes an alignment element 1714 which may be one or more struts which extend vertically upward and substantially parallel to the prosthetic valve. The alignment element 1714 may include radiopaque markers (not illustrated) to facilitate visualization under fluoroscopy. The alignment element helps the physician to align the prosthetic valve with the native mitral valve anatomy, as will be discussed later.

Disposed under the atrial skirt region is the annular region 1720 which also has a collapsed configuration for delivery, and an expanded configuration for anchoring the prosthetic valve along the native valve annulus. The annular region is also comprised of a plurality of interconnected struts that form a series of cells, preferably closed. Suture holes 1721 in some of the struts allow tissue or other coverings (not illustrated) to be attached to the annular region. Covering all or a portion of the anchor with tissue or another covering helps seal the anchor against the heart valve and adjacent tissue, thereby ensuring that blood is funneled through the valve, and not around it. The annular region may be cylindrical, but in preferred embodiments has a posterior portion 1704 which is circular, and an anterior portion 1702 which is flat, thereby forming a D-shaped cross-section. This D-shaped cross-section conforms better to the native mitral valve anatomy without obstructing blood flow in other areas of the heart.

The lower portion of the prosthetic valve includes the ventricular skirt region 1728. The ventricular skirt region also has a collapsed configuration for delivery, and an expanded configuration for anchoring. It is formed from a plurality of interconnected struts that form a series of cells, preferably closed, that can radially expand. The ventricular skirt in the expanded configuration anchors the prosthetic valve to the ventricle by expanding against the native mitral valve leaflets. Optional barbs 1723 in the ventricular skirt may be used to further help anchor the prosthetic valve into the ventricular tissue. Barbs may optionally also be included in the atrial skirt portion as well as the annular region of the anchor. Additionally, optional suture holes 1721 in the ventricular skirt may be used to help suture tissue or another material to the ventricular skirt region, similarly as discussed above. The anterior 1702 portion of the ventricular skirt may be flat, and the posterior 1704 portion of the ventricular skirt may be circular, similarly forming a D-shaped cross-section to anchor and conform to the native anatomy without obstructing other portions of the heart. Also, the lower portions of the ventricular skirt serve as deployment control regions since the lower portions can remain sheathed thereby constraining the ventricular skirt from radial expansion until after the optional ventricular trigonal tabs and posterior tab have expanded, as will be explained in greater detail below.

The ventricular skirt portion may optionally also include a pair of ventricular trigonal tabs 1724 on the anterior portion of the anchor (only 1 visible in this view) for helping to anchor the prosthetic valve as will be discussed in greater detail below. The ventricular skirt may also optionally include a posterior tab 1726 on a posterior portion 1704 of the ventricular skirt for anchoring the prosthetic valve to a posterior portion of the annulus. The trigonal tabs 1724 or the posterior tab 1726 are tabs that extend radially outward from the anchor, and they are inclined upward in the upstream direction.

The actual valve mechanism is formed from three commissures posts (also referred to as commissures) 1713 which extend radially inward toward the central axis of the anchor in a funnel or cone-like shape. The commissures 1713 are formed from a plurality of interconnected struts that create the triangular shaped commissures. The struts of the commissures may include one or more suture holes 1721 that allow tissue or a synthetic material to be attached to the commissures. In this exemplary embodiment, the valve is a tricuspid valve, therefore it includes three commissures 1713. The tips of the commissures may include a commissure tab 1712 (also referred to as a tab) for engaging a delivery catheter. In this embodiment, the tabs have enlarged head regions connected to a narrower neck, forming a mushroom-like shape. The commissures may be biased in any position, but preferably angle inward slightly toward the central axis of the prosthetic valve so that retrograde blood flow forces the commissures into apposition with one another to close the valve, and antegrade blood flow pushes the commissures radially outward, to fully open the valve. FIG. 17B is a top view illustrating the prosthetic valve of FIG. 17A from the atrial side, and shows the preferred D-shaped cross-section.

FIG. 18A illustrates the prosthetic mitral valve of FIGS. 17A-17B with a covering 1770 coupled to portions of the anchor with suture 1772. This view is taken from an atrial perspective. In this embodiment, the covering is preferably pericardium which may come from a number of sources as disclosed elsewhere in this specification. In alternative embodiments, the covering may be a polymer such as Dacron polyester, ePTFE, or another synthetic material. The covering is preferably disposed over the annular region 1720 and the ventricular skirt region 1728, and in some embodiments the anterior ventricular trigonal 1724 tabs and the ventricular posterior tab 1730 may also be covered with the same or a different material. The covering helps seal the anchor against the adjacent tissue so that blood funnels through the valve mechanism. In this embodiment, the atrial skirt is left uncovered, as well as tabs 1724, 1730. Additionally, radiopaque markers 1714a form a portion of the alignment element and facilitate visualization of the prosthetic valve under fluoroscopy which is important during alignment of the valve.

Figure 18B:
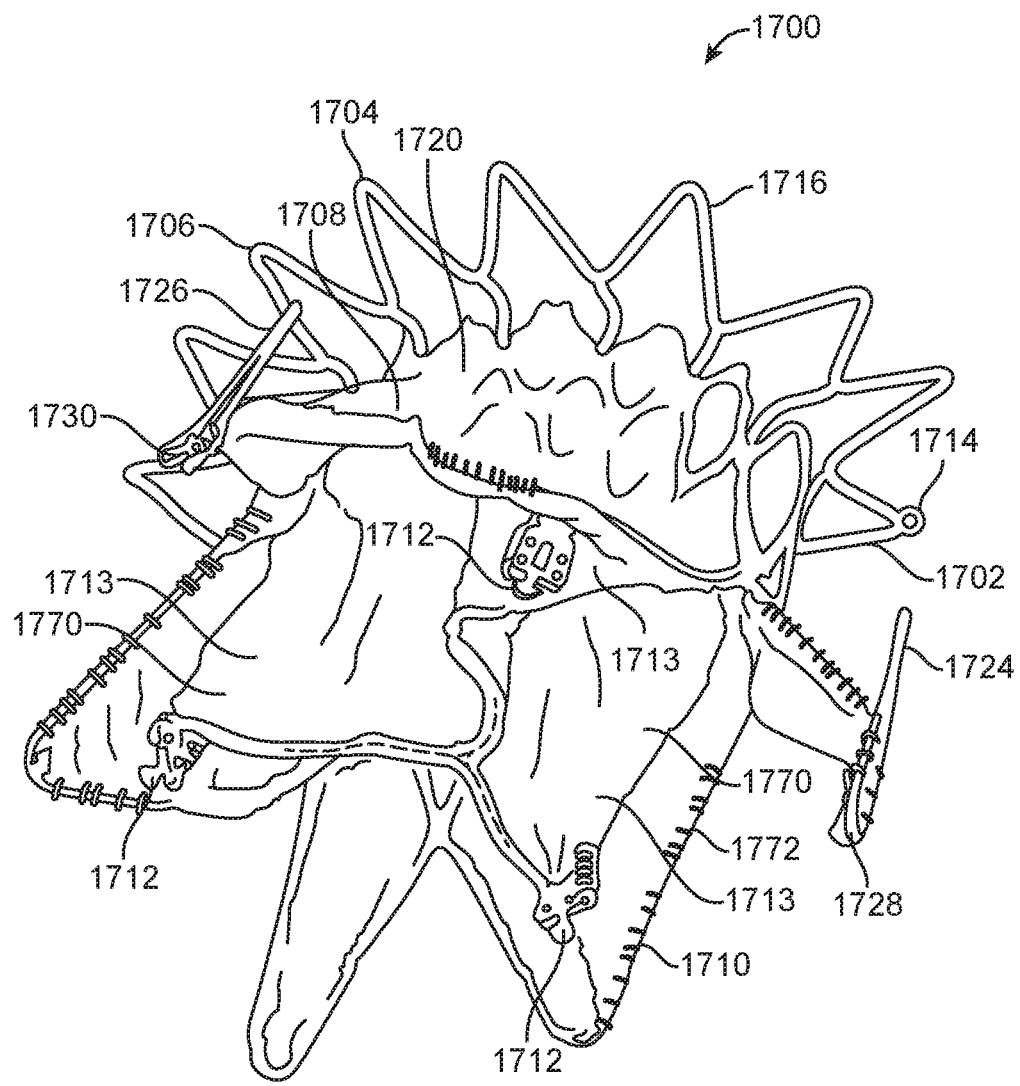
FIG. 18B illustrates a perspective view of the prosthetic valve in FIG. 17A.

FIG. 18B is a perspective view of the prosthetic mitral valve seen in FIG. 18A, as seen from the ventricle. The struts of the valve commissures are covered with the same material or a different material as the annular and ventricular regions as discussed above, thereby forming the tricuspid valve leaflets 1713. FIG. 18B shows the valve in the closed configuration where the three leaflets are engaged with one another preventing retrograde blood flow. Commissure tabs 1712 remain uncovered and allow the commissures to be coupled with a delivery device as will be explained below. The prosthetic valve in FIGS. 18A-18B may be sterilized so they are suitable for implantation in a patient using methods known in the art.

While preferred embodiments of the present invention have been shown and described herein, it will be obvious to those skilled in the art that such embodiments are provided by way of example only. For example, any capsule may be used in any delivery catheter, delivery system, or method of delivering a prosthesis as disclosed herein. Similarly, any prosthesis or prosthetic valve may be used with any delivery catheter, delivery system, or method of delivering a prosthesis as disclosed herein. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A delivery system for delivering a prosthesis to a target treatment area, the system comprising:
   an inner guidewire catheter having a proximal end, a distal end, and a lumen extending therebetween, the lumen sized to slidably receive a guidewire;
   a distal capsule coupled to the distal end of the inner guidewire catheter, wherein the distal capsule comprises an inner channel sized to receive the prosthesis;
   a bell catheter slidably disposed over the inner guidewire catheter, the bell catheter having a bell element adjacent a distal end of the bell catheter;
   an anchor catheter slidably disposed over the bell catheter, the anchor catheter having an anchor element adjacent a distal end of the anchor catheter and configured to engage the prosthesis, and wherein the bell element constrains the prosthesis into engagement with the anchor element;
   a sheath catheter slidably disposed over the anchor catheter, the sheath catheter having a proximal end and a distal end;
   a proximal capsule coupled to the distal end of the sheath catheter, wherein the proximal capsule comprises an inner channel sized to receive the prosthesis; and
   an actuator mechanism comprising a first rotational actuator element and a second rotational actuator element, wherein the first rotational actuator element is operably coupled to both the inner guidewire catheter and the bell catheter, wherein actuation of the first rotational actuator element in a first direction moves the distal capsule toward the proximal capsule, and wherein actuation of the first rotational actuator element in a second direction opposite the first direction moves the distal capsule away from the proximal capsule and moves the bell element away from the anchor element thereby removing a constraint from the prosthesis and allowing the prosthesis to expand, and
   wherein the second rotational actuator element is operably coupled to the sheath catheter, wherein actuation of the second rotational actuator element in one direction moves the proximal capsule away from the distal capsule, and wherein actuation of the second rotational actuator element in another direction opposite the one direction moves the proximal capsule into engagement with the distal capsule thereby enclosing the prosthesis therein.

2. The system of claim 1, further comprising a steerable catheter having an actuator mechanism comprising a rotatable knob, wherein the inner guidewire catheter, the bell catheter, the anchor catheter, and the sheath catheter are slidably disposed in the steerable catheter, and wherein actuation of the rotatable knob steers the steerable catheter, thereby steering the inner guidewire catheter, the bell catheter, the anchor catheter, and the sheath catheter.

3. The system of claim 2, wherein the steerable catheter comprises a plurality of pull wires coupled thereto, and wherein actuation of the rotatable knob moves the plurality of wires thereby steering the steerable catheter.

4. The system of claim 1, further comprising a handle coupled to a proximal portion of the delivery system, the actuator mechanism coupled to the handle.

5. The system of claim 4, wherein the first and the second rotational actuator elements each comprise a rotatable thumbwheel.

6. The system of claim 1, wherein the distal capsule comprises an expandable member.

7. The system of claim 6, wherein the expandable member comprises a stent or a balloon.

8. The system of claim 1, wherein the distal capsule comprises a corrugated region.

9. The system of claim 1, wherein the distal capsule comprises a plurality of hinged splines configured to radially expand at the hinge when compression is applied to the plurality of hinged splines.

10. The system of claim 1, wherein the distal capsule comprises proximal portion, a distal portion, and a plurality of filaments, and wherein movement of the plurality filaments moves the proximal portion relative to the distal portion thereby increasing or decreasing a length of the distal capsule.

11. The system of claim 1, further comprising the prosthesis, and wherein the prosthesis is a prosthetic mitral valve.

12. A method for delivering a prosthesis to a target treatment area, the method comprising:
providing a delivery system having a distal capsule coupled to an inner guidewire catheter and a proximal capsule coupled to a sheath catheter, a bell catheter having a bell element disposed adjacent a distal end of the bell catheter, an anchor catheter having an anchor element adjacent a distal end of the anchor catheter, and a sheath catheter having a proximal capsule coupled to a distal end of the sheath catheter;
actuating an actuation mechanism comprising a first rotational actuator element and a second rotational actuator element, wherein the actuating comprises actuating the first rotational actuator element in a first direction thereby moving the proximal capsule toward the distal capsule, and wherein the actuating further comprises actuating the first rotational actuator element in a second direction opposite the first direction thereby moving the proximal capsule away from the distal capsule and moving the bell element away from the anchor element, and
wherein the actuating further comprises actuating the second rotational actuator element in one direction thereby moving the proximal capsule away from the distal capsule, and wherein the actuating further comprises actuating the second rotational actuator element in another direction opposite the one direction thereby moving the proximal capsule into engagement with the distal capsule thereby enclosing the prosthesis therein;
releasing the prosthesis disposed in the proximal and distal capsules; and
deploying the prosthesis in the target treatment area.

13. The method of claim 12, wherein the inner guidewire catheter is slidably disposed in the sheath catheter, and wherein actuating the first rotational actuator element moves the inner guidewire catheter relative to the sheath catheter.

14. The method of claim 12, wherein actuating the first rotational actuator element or the second rotational actuator element comprises rotating a thumbwheel.

15. The method of claim 12, further comprising steering the delivery system with a steerable catheter disposed over the delivery system.

16. The method of claim 15, wherein the steering comprises actuating an actuator mechanism comprising a rotatable knob operably coupled to the steerable catheter.

17. The method of claim 16, wherein actuating the actuator mechanism comprises moving a plurality of pull wires coupled to the rotatable knob and the steerable catheter.

18. The method of claim 12, wherein the distal capsule comprises an expandable member, the method further comprising radially expanding or radially collapsing the expandable member.

19. The method of claim 18, wherein the expandable member comprises a stent or a balloon.

20. The method of claim 12, wherein the distal capsule comprises a corrugated region, the method further comprising axially expanding or axially collapsing the corrugated region.

21. The method of claim 12, wherein the distal capsule comprises a plurality of hinged splines, the method further comprising radially expanding the hinged splines by applying compression thereto, or radially collapsing the hinged splines by applying tension thereto.

22. The method of claim 12, wherein the distal capsule comprises a proximal portion, a distal portion, and a plurality of filaments, the method further comprising moving the plurality of filaments thereby moving the distal capsule toward or away from the proximal capsule.

23. The method of claim 12, wherein the target treatment area is a native mitral valve.

24. The method of claim 12, wherein the prosthesis is a prosthetic mitral valve.

* * * * *

UNITED STATES PATENT AND TRADEMARK OFFICE
CERTIFICATE OF CORRECTION

PATENT NO. : 10,631,984 B2
APPLICATION NO. : 15/379748
DATED : April 28, 2020
INVENTOR(S) : Nyuli et al.

It is certified that error appears in the above-identified patent and that said Letters Patent is hereby corrected as shown below:

In the Specification

In Column 2, Line 2, after "prosthesis", insert --.--

In Column 6, Line 25, delete "7" and insert --6-- therefor

In Column 6, Line 43, delete "14" and insert --13-- therefor

In Column 11, Line 11, delete "a-side" and insert --A-side-- therefor

In Column 11, Line 11, delete "b-side" and insert --B-side-- therefor

In Column 11, Line 26, delete "a-side" and insert --A-side-- therefor

In Column 13, Line 52, delete "14," and insert --13,-- therefor

In Column 13, Line 67, delete "14" and insert --13-- therefor

In Column 14, Line 20, delete "14" and insert --13-- therefor

In Column 14, Line 44, delete "14" and insert --13-- therefor

In Column 15, Line 9, delete "14" and insert --13-- therefor

In the Claims

In Column 18, Line 61, in Claim 3, after "of", insert --pull--

Signed and Sealed this
Eighth Day of December, 2020

Andrei Iancu
*Director of the United States Patent and Trademark Office*

In Column 19, Line 12, in Claim 10, after "comprises", insert --a--

In Column 19, Line 13, in Claim 10, after "plurality", insert --of--